(12) United States Patent
Lambert

(10) Patent No.: US 8,535,107 B2
(45) Date of Patent: Sep. 17, 2013

(54) BIOPHYSICAL GEOENGINEERING COMPOSITIONS AND METHODS

(76) Inventor: Kal Karel Lambert, Hammond, OR (US)

( * ) Notice: Subject to any disclaimer, the term of this patent is extended or adjusted under 35 U.S.C. 154(b) by 97 days.

(21) Appl. No.: 13/225,885

(22) Filed: Sep. 6, 2011

(65) Prior Publication Data

US 2012/0011050 A1    Jan. 12, 2012

Related U.S. Application Data

(63) Continuation-in-part of application No. 12/463,409, filed on May 10, 2009, now Pat. No. 8,033,879, which is a continuation-in-part of application No. 12/404,691, filed on Mar. 16, 2009, now abandoned, which is a continuation-in-part of application No. 12/345,661, filed on Dec. 29, 2008, now abandoned.

(60) Provisional application No. 61/009,414, filed on Dec. 29, 2007.

(51) Int. Cl.
*B63B 22/00* (2006.01)
*B63B 39/10* (2006.01)

(52) U.S. Cl.
USPC .............................. 441/1; 114/234

(58) Field of Classification Search
USPC ..................... 441/1; 114/232, 234
See application file for complete search history.

(56) References Cited

U.S. PATENT DOCUMENTS

| | | | | |
|---|---|---|---|---|
| 6,056,919 A | * | 5/2000 | Markels, Jr. | 422/40 |
| 6,868,361 B2 | * | 3/2005 | Desa et al. | 702/156 |
| 8,033,879 B2 | * | 10/2011 | Lambert | 441/1 |
| 2005/0118122 A1 | * | 6/2005 | Simon et al. | 424/63 |
| 2006/0121166 A1 | * | 6/2006 | Jeckle | 426/395 |

* cited by examiner

*Primary Examiner* — Stephen Avila
(74) *Attorney, Agent, or Firm* — Lambert Patent Services, LLC

(57) ABSTRACT

Described here are compositions, methods and apparatus for biological and physical geoengineering. Disclosed are inorganic particles, prill, pucks, or floats for dispersal on a body of water. These compositions are found to A) increase yields for pelagic aquaculture, B) increase carbon sequestration, and C) provide immediate relief from global warming by directly increasing surface albedo, reducing sea surface temperatures, and indirectly by increasing cloud nucleation activity. A vertical spar buoy or spar buoy network is provided. The buoys or array of buoys are designed to resist wave motion while supporting an analytical platform below the 100-Year Horizon. Sedimentary deadfall through the 100-Year Horizon is measured and flux of fixed carbon is reported and validated. Issuance of validated carbon sequestration certificates and monetization and trading of those certificates are also described.

11 Claims, 19 Drawing Sheets

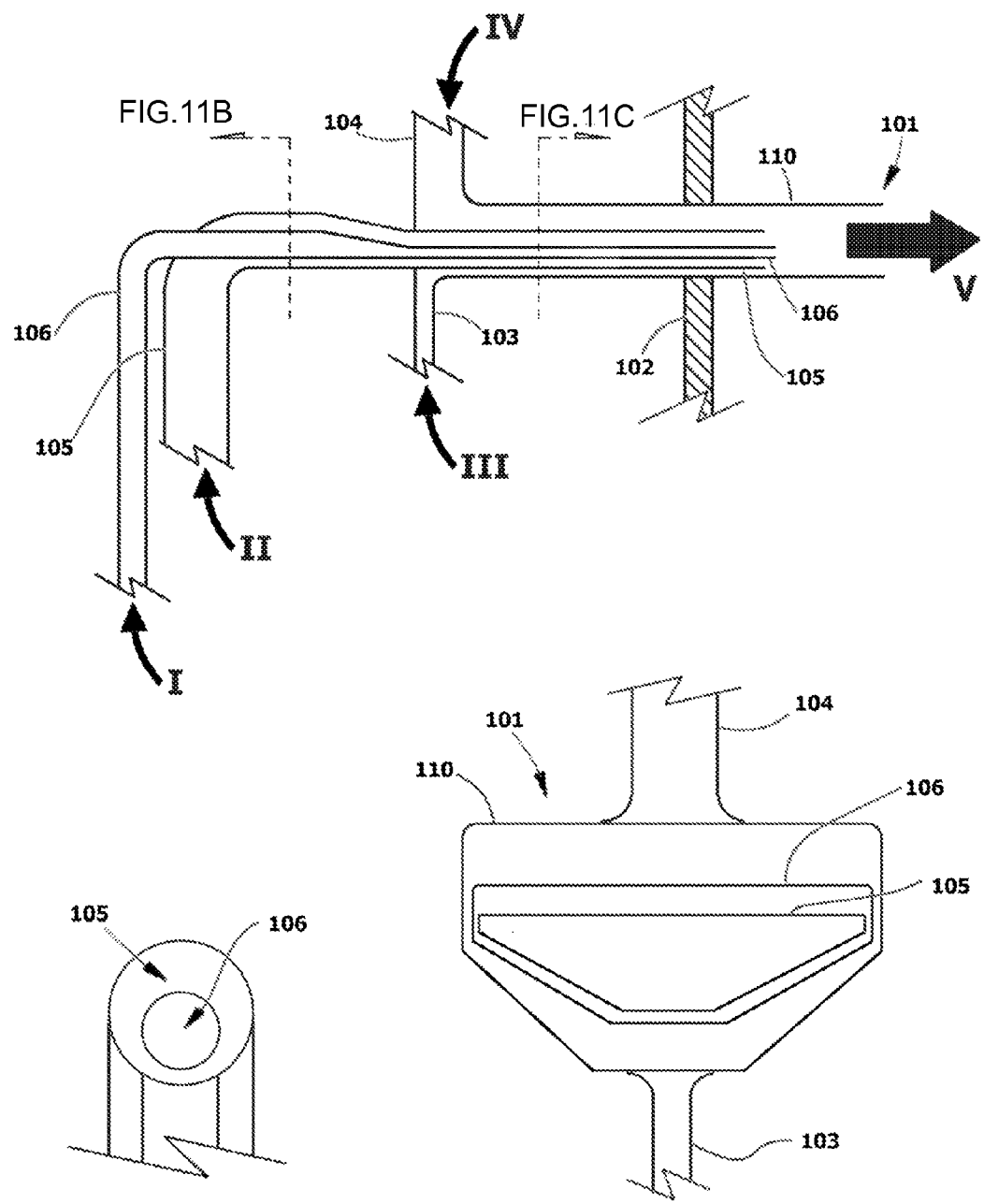

Fig. 24

TERRAFORMING FOR CO2 REMEDIATION: START

FIRST HAVING BUILT A NETWORK OR ARRAY OF SPAR BUOYS FOR ENCLOSING A SURFACE OF AN OCEAN;

DISPERSING A BUOYANT INORGANIC COMPOSITION WITHIN THE ENCLOSED SURFACE AT A PARTIAL FILL FACTOR, THE COMPOSITION HAVING A TOPOLOGY WITH MICROSCOPIC AND MACROSCOPIC NICHES;

SUSPENDING FROM THE NETWORK OR ARRAY OF SPAR BUOYS A SPACE FRAME DEFINING A 100 YEAR HORIZON AT A DEPTH OF 100 M;

MOUNTING AN INSTRUMENT PACKAGE ON THE SPACE FRAME FOR MEASURING SEDIMENTARY DEADFALL THROUGH THE 100 YEAR HORIZON;

MEASURING AND INTEGRATING FLUX OF SEQUESTERED CARBON PER UNIT TIME;

VALIDATING FLUX OF SEQUESTERED CARBON CROSSING 100 YEAR HORIZON; AND

ISSUING ONE OR MORE MONETIZABLE OR TRADABLE CARBON SEQUESTRATION CERTIFICATES, WHEREIN EACH CERTIFICATE HAS A DENOMINATION EQUIVALENT TO A VALIDATED AMOUNT OF SEQUESTERED CARBON AS CO2 IN THE SEDIMENTARY DEADFALL AS MEASURED HEREBY.

CONTINUING FOR EFFECT

BIOPHYSICAL GEOENGINEERING COMPOSITIONS AND METHODS

PRIORITY DOCUMENTS

This application is a continuation-in-part, and claims the benefit of priority under 35 U.S.C. §120, of U.S. patent application Ser. No. 12/463,409 filed on May 10, 2009, now U.S. Pat. No. 8,033,879 issued Oct. 11, 2011, which is a continuation-in-part of U.S. patent Ser. No. 12/404,691 filed on Mar. 16, 2009, now abandoned, which is a Continuation-in-Part claiming benefit of priority under 35 U.S.C. §120 from U.S. patent application Ser. No. 12/345,661 filed Dec. 29, 2008, now abandoned, which is a non-provisional application claiming benefit of priority under 35 U.S.C. §119(e) from U.S. Provisional Patent Application Ser. No. 61/009,414, filed Dec. 29, 2007; all said priority documents are incorporated herein in entirety by reference.

FIELD OF THE INVENTION

The invention is an apparatus and method for engineering planetary temperature by remediating $CO_2$ accumulation in the atmosphere to levels preceding the industrial revolution and by adjusting global albedo. Disclosed are methods for biophysical terraforming and means for funding those operations.

INTRODUCTION

Solar radiation striking the Earth's disk is in equilibrium with energy re-radiated as reflected light or as heat at longer wavelengths. The atmosphere traps a great deal of infrared radiation, warming the surface significantly above the black body temperature of the planet, which is a chilly $-20°$ C. However, there can be too much of a good thing. Reversing global warming requires re-adjusting the greenhouse gas composition of the atmosphere, but also proportionately removing energy from the planetary heat engine until the current sharp upturn in global surface temperature is brought to a halt.

The atmosphere is bidirectionally transparent to light in certain ranges of wavelengths known as "atmospheric windows". Reflected light at the planetary scale is thus a means to remove energy from the global heat balance. Albedo is a measure of the reflectivity of the planetary surface, which can be measured with satellite-mounted pyrometers. Changes in albedo result in very large scale net changes in the heat energy balance of the planet, and over short time frames. For example, IPCC models are now incorporating the area of solar panel installation worldwide—as an added heat source—into the assumptions for projected global warming, because conventional solar panels have very low albedo and re-radiate about 90% of incident light energy as black body radiation that is trapped by the atmosphere. Decreases in albedo are associated with planetary warming.

Conversely, increases in planetary albedo are expected to result in global cooling. Deliberate reconfiguration of planetary albedo is not without possible benefit, as evidenced by proposals under the aegis of the National Academy of Sciences to seed the high stratosphere with reflective particles. The problem is how to achieve a maximal benefit without causing harm. The work here begins with the question as to whether there is merit in more "down to earth" geoengineering works to modify albedo, and whether this can be done both economically (socio-ecological benefits exceeding direct and incidental costs of resource allocation) and safely. The answer is "yes" on both counts, as will be apparent on consideration of the following.

Similarly, anthropogenic injection of $CO_2$ into the atmosphere has resulted in an astonishing near doubling of the global atmospheric pool and increased $CO_2$ levels in the oceans. There is an urgent need to remediate these levels to pre-Industrial Revolution levels and to stabilize the levels until corrective restructuring of economic systems away from fossil fuels can be completed. $CO_2$ is a greenhouse gas, and carbon dioxide levels in the troposphere and the effects of albedo interact to result in global warming. The invention is an apparatus having the property of addressing both planetary hypercapnea and balancing solar insolation in an integrated solution that utilizes both biological and human-engineered systems to rebalance the planetary thermostat.

BACKGROUND

Direct climate intervention strategies on Earth (geoengineering, or more colloquially "terraforming") have not generally been viewed as a benefit, but more as a hazard. In light of current trends in climatology, it may be necessary to rethink these reservations. For starters, unintended geoengineering is well underway on a massive scale; there is convincing evidence of anthropogenic causality for climate change. Current anthropogenic release of carbon dioxide from fossil fuels and cement production is about 7 GtC/yr (7 metric gigatons as carbon) annually and may reach 12 GtC/yr by 2050, with probable net doubling of atmospheric $CO_2$ before the end of this century associated with inevitable greenhouse forcing the scale of which remains subject to debate (FIG. 1). Among the complications: overpopulation, violence, economic collapse, poverty, deforestation and desertification.

The scale of the problem is difficult to grasp. While well known to those skilled in the art, the direct implications of the past hundred years of "collateral" or "irrational" geoengineering will be reviewed here as a general background to the problem addressed by the invention.

Future atmospheric $CO_2$ concentrations in the year 2100 are projected by the IPCC to be in the range of 540 to 970 ppm, compared to only 370 ppm in the year 2000 and less than 280 ppm before the industrial revolution. Perhaps more impressive than concentration are the pool sizes themselves. Current atmospheric total $CO_2$ is about 750 $GtCO_2$, a doubling of the 360 $GtCO_2$ in the atmosphere less than 200 years ago.

Also of interest are the current flux rates. Fossil fuel export to the atmosphere is more than 6 GtC per year at present and is increasing sharply. Of this, about net 2 GtC is being absorbed in the oceans annually, about 30% of the carbon dioxide emissions from fossil fuel combustion. Since 1800, the ocean absorbed about 135 GtC carbon dioxide; as a result, the pH of the ocean is expected to be reduced by almost half a pH unit at the surface in the near term. Interestingly, higher rates of increase in atmospheric $CO_2$ tend to occur in El Niño years, as would be consistent with a Henry's Constant effect on the atmospheric/marine solubilized carbonate species equilibrium. Atmospheric $CO_2$ will continue to rise even if fossil fuel combustion is stopped tomorrow.

In addition, there is a high risk of positive feedback, the so-called "runaway" greenhouse effect. Total $CO_2$ pools incipiently releasable into the atmosphere (from long term sequestered stores in permafrost and methane hydrate deposits) as carbon are measurable in Teratons (i.e. exceeding $10^{12}$ tons as carbon). Since these pools are orders of magnitude larger than the existing total atmospheric pool, it should be clear that activities that could cause their release into the atmosphere are likely to result in mass extinctions. The trigger for melting permafrost and release of methane hydrate pools held in place by the ice caps may have already been pulled, but in light of the magnitude of the potential $CO_2$ release, it seems eminently sensible to act quickly to put a cork back in the bottle. Geoengineering is not a small thing to have done by accident, and it will not be a small thing to undo.

Therefore, there is an urgent need to re-engineer the planetary economy, both by restructuring industry, feedstocks, carbon footprints, and the like, but also by ameliorating ongoing damage to our shared "commons", the atmosphere and the oceans. This constitutes remedial terraforming, but is here termed "rational geoengineering" to better differentiate the science from the science fiction.

Rational approaches to geoengineering can be divided into two categories:biological and physical. Among the biological approaches are: carbon sequestration by marine fertilization and terrestrial or marine silviculture. Among the physical approaches are: injection of microparticulate reflectors into the stratosphere (as per the "Pinatubo Effect"); extraterrestrial solar parasols; carbon dioxide storage in geological formations (generally as carbonates); carbon dioxide storage in deep sea lakes (as liquified $CO_2$), and the like. The scale of any such project can be judged by comparison with more conventional alternatives: for example, an immediate roll-out of 6,700 new nuclear power plants (assuming 6.8 GWhr per plant, sufficient enriched uranium, and no waste in electrical distribution) would be required to zero out power consumption derived from fossil fuel alone (fossil fuel consumption is currently about 400 EJ or $4.6 \times 10^7$ GWHr annually and rising). At current cost of US$10B/plant, construction of an adequate number of nuclear power plants would amount to US$65 Trillion in present dollars and would take decades. Currently, less than 500 nuclear power plants are installed worldwide.

There are alternatives. Solar power is dependent on solar insolation, an essentially free energy source which averages out to about 160 $W/m^2$ (160 $J/s/m^2$) over the surface of the planet. Again taking 400 EJ as the target, replacing today's fossil fuel combustion with photovoltaic cells operating at 10% efficiency would require a solar panel array (or combined equivalent) the size of Venezuela, more than 400,000 $km^2$ if placed equatorially. Also a factor is the heat required for manufacture, such as by the Czochralski process, and periodic replacement of solar panels, capacity for which is practically nonexistent considering the scale. Current solar cell designs radiate heat as black bodies, emitting a great deal of waste heat, so that on the scale envisaged, heat emission from the required surface area of solar cells is likely to reach 2000 EJ annually (assuming 50% conversion to "new" heat), five times the current heat generated from fossil fuel combustion! Like water, conventional solar cells have the albedo of black asphalt. Taking solar insolation at the terrestrial surface as about 45 PW, the incidental heat pollution of the solar panels would be 4% of the overall global surface heat budget. Net flux of heat IN will exceed net heat OUT until a new global surface temperature at equilibrium is reached. The effect would be analogous to removing the high-albedo icesheet from Greenland and replacing it with a low-albedo asphalt surface, but positioned equatorially.

Measurements in support of a dramatic climate forcing by terrestrial albedo are readily found. In a widely cited paper by Palle (2004, Science 304:1299-1301), an observed decrease in global albedo of 0.02 was associated with an increased global heat budget of 6.8 $W/m^2$, a highly significant increase climatologically. Much of the decrease in global albedo is the result of anthropogenic changes in land use, vegetation, burning of forests, and deposition of soot upon snow. Installation of solar panels can be added to that list.

Currently, installed wind power on line is about 157 million MWHr or 0.34% of global demand. Within a few decades, because of the constancy of wind in Patagonia, more than 1.3 Trillion MWHr per year could be installed, or about 3.2% of global demand. But these areas of sustained strong wind are unusual and the estimates do not factor power losses through an electrical distribution grid or losses in a conversion process to liquid fuel for export.

Arable land required for biomass energy capture and conversion is estimated at anywhere from 13,700 to 32,000 $km^2$/EJ. To capture the equivalent of 400 EJ, perhaps $8 \times 10^6$ $km^2$ must be converted to cropland, an area the size of Australia, or about 5% of the earth's land mass. This does not factor in the overhead energy costs of farming, which should perhaps double the area needed. Currently, about $1.3 \times 10^6$ $km^2$ is under cultivation in the US for food crops. So again, the undertaking is beyond enormous—energy crops cannot simply replace food crops worldwide without major sociopolitical consequences. The irreplaceable and unsustainable bounty of readily available fossil fuels simply cannot be overstated.

Population extinction by economic pressure has also been considered, but the social dislocations of such a program pose considerable risks to those who would contemplate it, no matter what walls are constructed. In a recent article titled, "Guns beat Green", writer Naomi Kline, writing in the December 2007 *The Nation*, shows that market investments favoring a fortress mentality, private security for the wealthy and weapons at the borders, surpassed new investments in sustainable energy technologies. Weapons and security technologies received 6 Billion $US in venture capital in 2007 whereas green technologies received only 4.3 Billion $US, and the gap has been widening. Peak oil is on the near horizon, despite recent drastic downturns in global demand, but the consensus in the stock market seems to be that those with the guns will consume the last gallon of gas! Clearly the betting money is on economic Darwinism to solve the problem of climate change. Can we truly sustain a Maginot Line or Demilitarized Zone in the face of new and greater waves of hungry illegal immigrants at our borders? Can we fortify our communities and not be impacted by a global collapse of democratic values, commodities, currencies, and access to markets?

Clearly, no single program is feasible at the scale required. Conservation efforts, for example business metrics based on "carbon footprint", are laudible but not yet up to the Draconian task required to eliminate 400 EJ from the annual global energy budget. Although comforting, and in the short term profitable to some, recent innovations in carbon trading are far from meaningful net reductions, and are in fact a sort of shell game that in all likelihood most frequently attempts to obfuscate the scope of the problem.

Alternatives to the handling of fossil fuels have also been proposed. What is euphemistically termed "clean coal" technology, for example, proposes to inject by-product $CO_2$ from coal gasification or power production into sub-terrestrial strata such as depleted oil fields. While this sounds attractive, the energy fluxes of use of coal, even just those associated with processes for putative entombment of waste $CO_2$ are likely as not to result in a net planetary heat gain and are unsustainable.

Nonetheless, business as usual is clearly not an option, such a course posing unacceptable hazards and burdens for future generations. FIG. 1 suggests the current trend in global mean temperature, which is tied closely to $CO_2$ release into the atmosphere. Note that 2100 does not bring a plateau in the relentless rise in global mean temperature that started in the late $20^{th}$ century, and we are again forced to ask whether our lifestyle presages mass extinctions. The greenhouse effect that has been apparent since the first plots from Mauna Kea Observatory were released in 1970's must be stopped.

In addition to combustion of fossil fuels, other sources of greenhouse gases must be considered. Pre-industrially, deforestation accounted for about 75% of the total annual increase in atmospheric carbon dioxide, but is now only about 20%, having been swamped by rising fossil fuel combustion. Globally, the four activities responsible for most $CO_2$ emissions are: 1) fossil fuel combustion, 2) deforestation, 3) agriculture and 4) manufacture of Portland cement.

Conversion of native ecosystems to cropland or pasture continues to be associated with both soil deterioration and release from soil humus of up to perhaps 1.5 Tt of sequestered carbon, an ongoing process. Remaining fossil fuel reserves, importantly including coal, are estimated at over 5 Tt C (18 Tt $CO_2$), and most of this is being developed or evaluated for "exploitation", perhaps understandably given the market premium placed on the value of gasoline, which is only likely to rise. Not surprisingly then, use of fossil fuel reserves seems to be accelerating and there is tremendous pressure to bring untapped reserves to market, such as the Athabasca Tar sands and recently discovered fields under the melting arctic ice cap, in hopes of stimulating one final burst of prosperity. Psychology is a critical factor confounding the hard science of global warming, and there will be a need for temporary relief, a cooling off period, so that the reality of the situation can be fully assimilated and a sober commitment to a sustainable future can be engendered.

There had been an expectation for some time that a negative feedback mechanism in global climate would emerge, a sort of "Gaia-effect", perhaps in the form of increased oceanic albedo through cloud condensation nucleii as proposed by Robert Charlson of the University of Washington in 1987 (Nature 326:655-61). Speculatively, increased vulcanism associated with accelerated tectonic plate slippage may be that link. However, we can also expect the opposite—positive feedback effects. One such example is found in the expected effects of a meltdown of the West Antarctic ice sheet. Accounting for the rebound of the Earth's crust following relief from the weight of the ice sheet, and resulting shift in polar axis of rotation, the predicted 5 m sea level rise is expected to be even higher, perhaps 6.3 m, in the northern hemisphere, where the bulk of the continents are located (Mitrovica, J X et al. 2009. The sea level fingerprint of West Antarctic collapse. Science 323:753). Increased ocean surface area resulting from continental flooding can be expected to dramatically reduce global albedo over large areas, in aggregate reducing reflected heat and increasing the temperature "set point" of the planet. A similar positive-feedback potential of sequestered carbon in permafrost and methane hydrates (pool size >1 TtC) has already been mentioned.

Divine intervention aside, an exponential reverse J-curve in economic activity and population is the more likely negative feedback we can expect in the short term. Deceases in human activity have been associated with periods of relief. For example, changes in agriculture and silviculture practice across northern Asia following the dissolution of the Soviet Union resulted in measurable decreases in radiative forcing due to greenhouse gas heating (i.e., decreases in livestock husbandry resulting in decreased production of methane) and increases in forest carbon dioxide sinks (by decreases in timber harvesting). Ruddiman has proposed a related argument associating cooling trends observed following first contact of Europeans and Native Americans. Similarly, any slowing of global economic activity due to the present day banking crisis will likely reduce carbon dioxide output. If this can be managed while avoiding social instability or complete economic collapse, then the benefit will be permanent. At the very least, a decrease in carbon dioxide output and global warming superimposed on a downturn in human economic activity will relieve any lingering doubts in the minds of planners that greenhouse warming is anthropogenic at its roots.

Thus by the process of elimination of alternatives recited here, geoengineering must be seriously considered as part of any comprehensive effort to solve the problem—absent any compelling argument to the contrary. Two arguments against rational geoengineering are commonly made. First that the ecological risks are unacceptable. Second that any ameliorative action taken would ease the pressure to make the hard decisions needed to develop a sustainable energy economy. Both these arguments will likely weaken when and if global warming enters a "runaway" phase. Arguments about ecological risk must seem hypocritical even now given the reckless behaviors that have produced the crisis. In short, it seems inevitable that resistance to rational terraforming will wilt when temperatures or sea level spikes sharply. Therefore the "roll-out" of any terraforming device must have a short lead time and quickly become effective. It is reasonable to want to prepare for this while organized economic activity on a global scale is still possible. Preliminary studies undertaken at this time, undertaken to ensure that an effective response will be available when the political urgency becomes compelling, seem entirely defensible and in fact of the highest priority.

Optimally, a geoengineering device and method for amelioration of the global heat budget and greenhouse effect might be required for a few years or a decade to blunt peak emissions, following which we ultimately make more sustainable choices to fuel the economy. The geoengineering device and method would thus simply be a means for gaining the time needed for committed change, and conveniently, would then dissipate and vanish without further intervention. Thus rational geoengineering is seen not as an artifice to evade, but rather as a potential borrowing of time to survive an incipient crisis. The needed research can be funded "for profit" or by the foresight of governments as part of a "New Deal"-style spending package, but the latter is more likely given the lack of international law in this area.

Some work toward marine geoengineering was initiated on a small scale as early as 1993, and the results have been confirmed in numerous subsequent studies. As set forth in detail at www.palomar.edu/oceanography/iron.htm (accessed 30 Jan. 2007), the IronEx I research vessel Columbus Iselin set out to sea in 1993 fitted with a portable laboratory and loaded with 21 barrels of blue-green iron granules (about 0.5 t of ferric sulfate). The mineral was dissolved in seawater at the test site and dispersed in a location SW of the Galopagos Islands. Application resulted in increase of iron from about 20-50 pM to about 1-2 nM and a three-fold increase in phytoplankton (measured as chlorophyll) in the treated area. The biological enrichment resulted in transient sequestration of about 300 t carbon dioxide over a two week period. This experiment generated a tremendous debate and was repeated in 1995, with yet better results, stimulating a 30× increase in surface chlorophyll, principally in the form of diatoms, but also higher trophic levels, as had been predicted. An estimated 9,100 t of carbon dioxide was drawn down. Encouragingly, follow up work has not demonstrated significant collateral production of NOX or methane.

The effort was originated in 1986 by John Martin of Moss Landing Marine Laboratories, and was first disclosed in response to a presentation by Bruce Frost of the University of Washington, who had noted that some ocean areas were unexpectedly phytoplankton poor (the "high-nitrate/low chlorophyll" oceans), for example the Pacific equatorial belt extending east from Irian Jaya to Peru and the roaring 40's, the belt of water surrounding Antarctica. Martin had suggested that biological productivity was limited by iron availability, and that iron fertilization would result in a phytoplankton bloom and could be used as a means to reduce the greenhouse effect (which was already well understood in scientific circles by the 1980's) by sequestering carbon dioxide. See for example, Martin et al. 1990. Glacial-interglacial $CO_2$ change: The iron hypothesis. Paleoceanography 5:1-13 and discussions [www.palomar.edu/oceanography/iron.htm] of the period. Use of marine fertilization with iron to stimulate marine productivity and sequester $CO_2$ is thus not a novel concept and a first full, clear and definite conception was articulated in the mid-1980s.

In the second Iron-Ex expedition, in 1996, headed by Kenneth Coale, it was noted that the redox state of the inorganic iron was important, ferric iron precipitating rapidly as the hydroxide and exiting the photic zone. Nonetheless, a dense and somewhat anoxic phytoplankton bloom was observed and documented.

Other experiments of this same kind have since been published (see Tsuda A et al. 2003. A mesoscale iron enrichment in the western subarctic Pacific induces a large centric diatom bloom. Science 3009:58-61; Markels and Barber. 2001. Sequestration of $CO_2$ by ocean fertilization. Poster Presentation for NETL Conference on Carbon Sequestration; Boyd P W et al. 2000. A mesoscale phytoplankton bloom in the polar Southern Ocean stimulated by iron fertilization. Nature. 407: 695-702; Coale K H et al. 2004. Southern Ocean iron enrichment experiment: carbon cycling in high- and low-Si waters. Science 304:408-14; Boyd P W et al. 2004. The decline and fate of an iron-induced subarctic phytoplankton bloom. Nature 428:549-53). A total of 12 experiments were recently reviewed by Boyd (Boyd P W et al. 2007. Mesoscale iron enrichment experiments 1993-2005: synthesis and future directions. Science 315:612-7). A newsworthy update was recently published in Science (318:1368-70, 2008).

Patent literature has also accumulated, beginning with a 28 Apr. 1994 filing by Markels (U.S. Pat. No. 5,433,173), which claimed a method for first measuring nutrients in seawater, of then adding any missing nutrients to the ocean, and finally harvesting the increased production as seafood. Use of a "float material" such as rice hulls, wheat chaff, ground corn cobs [and] peanut hulls was proposed as a form of fertilizer that would dissolve in the surface over a period of days, or perhaps as long as a week. The detailed description involved shipboard pumping of a liquid fertilizer composed primarily of iron with some phosphates and nitrates, and disclosed "that almost certainly algae will grow". It can be said that John Martin unequivocally articulated that same assertion almost a decade earlier. Markels' patent was awarded with narrow claims.

This was followed by U.S. Pat. No. 5,535,701, which cited one of the Martin papers (Martin et al. 1994. Testing the iron hypothesis in ecosystems of the equatorial Pacific Ocean. Nature 371:123-129). In the second filing, the method was supplemented by further providing a nitrogen-fixing organism with the fertilizer. As examples of compositions for such use of fertilizers, starch mixtures with iron were suggested. Compositions were again not claimed.

In U.S. Pat. No. 5,967,087, Markels claimed a method for increasing seafood production, where the fertilizer contains iron in a chelated form so that the iron does not precipitate from the photic zone as hydroxides. Compositions for the method were disclosed. The compositions included binders such as plastic, wax, or starch to provide timed release over two weeks of the fertilizer, and a plastic pellet matrix compounded to float by attaching the fertilizing matrix to a float material such as glass bubbles, plastic foam, or by introducing gas bubbles into the fertilizer pellets during manufacture. The matrix selected for attaching the fertilizing elements to the float element or for introducing gas bubbles into the fertilizer pellets was taught to be a plastic matrix, or optionally a wax (Col 4 lines 48-65). Again the timed release matrix disclosed was selected to dissolve in two weeks or less, and in subsequent disclosures, pulse fertilization at intervals greater than 30 days was reported as preferable.

In 2000 and 2002, two US patents issued to Markels claiming methods for sequestering carbon dioxide by ocean fertilization. In U.S. Pat. No. 6,056,919 the steps of the claimed method involve testing to identify a missing nutrient, applying a fertilizer to supply the nutrient, limiting the bloom by applying the fertilizer in pulses, and measuring the amount of carbon dioxide sequestered. Pulse application at intervals of greater than 30 days (see independent claims 1 and 15) was taught to limit anoxia in the phytoplankton blooms. It is known that micrograzing and eutrophication result in lessened carbon sequestration.

In U.S. Pat. No. 6,440,367, methods of applying iron chelates to the ocean were claimed for sequestration of carbon dioxide. Disclosed was an iron:lignin chelate. In this case, and all such related cases, the teachings teach away from the use of the less expensive insoluble mineral forms, which would be expected to precipitate if mixed into the ocean—an unsolved problem.

US Patent Appl. 2002/0023593 relates again to methods of increasing seafood production. Claims 1, 10 and 14 summarize the relevant teachings as to compositions: [a method wherein] first, iron is to be supplied as a chelate, and secondly, "said second fertilizer is in the form of pellets, and said pellets comprise a float material selected from gas bubbles and/or low density materials, and said pellets further comprise a binder selected from plastic, wax, high molecular weight starch, or a combination thereof". Any such composition consists of an organic binder, a float material, and an iron chelate, but note that the claims relate strictly to methods, and that in all the claims in this series, the steps are always to measure the nutrient concentrations in seawater, to determine the limiting nutrient, and then to supply that nutrient, the substance of what John Martin had proposed for iron-poor oceans. A method in which the limiting nutrient is not measured is not claimed.

As for compositions, the methods of the prior art teach solubilized minerals, chelates, and a narrow genus of pellet matrices selected from the list of organic chemicals consisting of plastic, wax, and starch. All such pellets contain an organic binder.

However, selection of an organic matrix is problematic in that the named materials are responsible for very high levels of biological oxygen demand, starch for example, thus promoting the growth of heterotrophs, particularly bacteria not native to the pelagic ocean, which will certainly exacerbate oxygen depletion in the underlying water and reduce carbon sequestration by resolubilizing any carbon dioxide fixed by primary producers. Plastic materials are also a major pollutant in the world's oceans and typically contain carcinogenic plasticizers. Wax is not expected to form monodisperse sustained-release pellets absent a surfactant and is difficult to handle. Other objections to the selections taught by Markels could be elaborated here. Organic binders will likely have a highly negative effect on ocean surface chemistry by disintegrating into short chain oils and organic polymers, and thus displacing native surfactants, chelators, siderophores, and the like from the neuston, which is a critical environment in pelagic ocean biology.

Similar problems are found with organic materials as a genus, such as the rice crispies and peanut hulls proposed as float materials. While the use of "glass bubbles" as a float material is attractive, current supplies of hollow glass microspheres, as the term "bubble" would be understood by one skilled in the arts, are expensive and the Markels disclosures teach an organic binder or matrix selected from plastic, wax and starch wherein the glass bubbles are added to the matrix solely for buoyancy. The work to date has also been criticized by others because supplementation with the limiting nutrient in one area will necessarily deplete the water body of other nutrients, which then become limiting as the water body moves out of the test area. In other words, while some hope to profit by fertilizing within a fence, the profit is robbed from areas outside the fence, a classical retelling of the tragedy of the commons. As an example, see U.S. Pat. No. 6,729,063, where the problem is made transparent. The method of first measuring nutrient concentrations in a body of water and then supplementing said body of water with an excess of the most needed nutrient or nutrients is thus fundamentally flawed, and increases productivity in the test site by robbing the productivity of adjoining areas. To the extent that this is also the Martin Iron Hypothesis, the hypothesis has been highly instructive and successful, but is flawed as a method for rational geoengineering.

In short, the prior art has taught inter alia that high bioavailability of the nutrient supplement is preferable, that formation of insoluble hydroxides of metals is prevented by chelation, and that pulse administration is necessary to prevent blooms. But what if there was a better way?

There remains a need for a composition of a marine fertilizer formulated to overcome the above disadvantages and to provide for sustained release of a balanced palette of micronutrients over a growing season or more. Such a composition may be of benefit in increasing harvestable species while also sequestering atmospheric carbon dioxide. Valuable characteristics of such a composition include provision of increased surface area for habitat, providing spatial richness of niches as well as a nutritive leachate (noting that surface chemistry and biochemistry is sufficient, i.e. not requiring exogenous chelators, to ensure that bioactive mineral forms are released at equilibrium rates for uptake). Changes in redox species of a mineral are achieved simply by supplying a surface on which they may be bound, eliminating the need for what is meant in the chemical art by "chelators". Because surfaces alone also result in "passive" shifts in the equilibrium concentrations of the redox species toward slow sustained release of soluble species and further supply habitat niches for microbiota that further modify the release of those mineral species as native organic complexes, synergic accumulation of higher trophic levels of biomass is highly favored. This biomass can result in macro-sedimentation or can be harvested, or a combination of both, and is net new production. These compositions are buoyant to ensure a $T_{0.5}$ of greater than 3-6 months in the photic zone and are optionally reflective on a skyward surface so as to provide immediate SST cooling. Light is not limiting except seasonally at polar latitudes!

An area of particular interest involves the design of nutrient formulations to promote the growth of particular foodchains and the associated primary producers. For $CO_2$ sequestration, for example, it may be preferable to select a formulation that promotes the growth of coccolithophorids in preference to diatoms. Phaeocystis antarctica takes up twice as much $CO_2$ per mole of $PO_4$ removed than do diatoms, it has been reported. Foraminifera deposit calcium carbonate shells, a preferred sequestration and deposition mineral. For cloud formation, it may be useful to increase dimethylsulfide production by selection of an enrichment medium that increases expression of the prymnesiophyte-microzooplankton envirotype (see Boyd P W et al. 2000. A mesoscale phytoplankton bloom in the polar southern ocean stimulated by iron fertilization. Nature 407:695-702). At some surface fill factors, gas exchange is reduced, but this can be adjusted or even overcome by physical design of the formulation. Referring again to the CLAW hypothesis formulated by Charlson, Lovelok, Andreae and Warren (Nature 326:655-661, 1987): dimethylsulfide (DMS) is thought to play a role in regulating the temperature of the planet by regulation of kumogenesis and associated cloud albedo. Dimethylsulfonio-propionate (DMSP) is biologically converted to DMS (a volatile compound), the main source of organic sulfur in the atmosphere above the oceans. Phytoplankton produce DMS that escapes into the atmosphere where it is oxidized to sulfuric acid, which acts as a nucleus for the condensation of water, and ultimately contributes to the albedo of the planet. According to the hypothesis, when cloud albedo increases, less solar radiation reaches the microbial plankton populations resulting in less photosynthesis and less DMS production, thereby creating a feedback loop that modulates the Earth's temperature [not allowing for the limiting effects of nutrients other than sulfur, which must complicate the model]. Experiments have shown that if the mixed layer depth is very shallow, then almost 100% of DMSP is converted into DMS, and as the mixed layer depth increases this value goes down. Using the mixed layer depth, chlorophyll concentrations and the DMS relationship, predicted DMS concentrations were nicely correlated with the real DMS concentrations in work by Rafel Simó and colleagues reported in Nature in 1999.

Provision of habitat in the form of bioactive surface area also has the effect of increasing trophic levels in rough proportion to the area and niche size of the habitat, a scalar porosity factor with a fractal dimension.

In contrast, current solution fertilization methods result in increases in dissolved organic carbon, picoplankton and, if sustained, transient populations of micro-grazers such as copepods. The fecal sediment fall is thus a "micro-sediment" with poor sedimentation characteristics, that is rapidly re-solubilized as $CO_2$ and organic acids by the action of heterotrophs. It is well established that pelagic "microzooplankton" are the principle grazers on marine phytoplankton (Billett, D et al. 1983. Seasonal sedimentation of phytoplankton to the deep-sea benthos. Nature 302:520-522; Ryther, J H. 1969. Photosynthesis and fish production in the sea. Science 166:72-76; Falkowski, P G et al. 2000. The global carbon cycle: a test of our knowledge of the Earth as a system. Science 290:291-294; Turner, J T et al. 2000. Accumulation of red tide toxins in larger size fractions of zooplankton assemblages from Massachusetts Bay, USA. Mar Ecol Prog Ser, 203:95-107; Smayda, TJ. 1970. The suspension and sinking of phytoplankton in the sea. Oceanogr Mar Biol Ann Rev 8:353-414; Irwin A J et al. 2006. Scaling-up from nutrient physiology to the size-structure of phytoplankton communities. J Plankton Res 28:459-471; Richardson, T. and Jackson, G. 2007. Small phytoplankton and carbon export from the surface ocean. Science, 315:838; Zarauz L et al. 2009. Changes in plankton size structure and composition, during the generation of a phytoplankton bloom, in the central Cantabrian sea. J Plankton Res 31:193-207). Micro-sediment sinks more slowly and is more likely to be resolubilized. The result is that relatively little micro-sediment crosses the "100-Year Horizon" at depth as required for permanent sequestration. As disclosed here, this can be seen principally as an effect of habitat size, and the primary geoengineering intervention that can increase the size and quantity of sediment is not nutrient level but instead habitat size, which effectively correlates with size of organism and number of trophic levels. With provision for habitat and nutrient levels capable of supporting higher trophic levels as taught here, "macro-sediment" is obtained, and there are associated significant increases in $CO_2$-derived organic matter descending below the 100-Year Horizon. Not only is net productivity increased, but the quality of the deep ocean fixed carbon efflux (or "biological pump") is improved.

Many oceans are "deserts", having relatively low biological net productivity. Ocean productivity in the form of net biological carbon assimilation is variously estimated at 36-48 GtC/yr, globally in aggregate, an impressive number. This marine productivity is about half of all global productivity, but is spread over an area of about $361 \times 10^6$ km$^2$ (almost three times the area of terrestrial ecosystems). Corridors of higher productivity tend to be localized, and a method for increasing productivity in less productive areas of the ocean has been long sought. As discussed above, nutrient limitation is the primary throttle on marine productivity over much of this ocean area. Ocean warming has also been correlated with decreases in ocean primary productivity. Therefore, a capacity to cool oceanic hot spots is also of interest in a research program into marine productivity.

The compositions and methods of the present invention bring welcome synergy to these convergent interests: global warming, marine productivity, and carbon sequestration. A combination of modalities—modification of global albedo and enhancements in marine productivity with associated increases in sedimentary lithification of atmospheric $CO_2$—addresses the global climate crisis in multiple ways. There is a need for a solution that overcomes the dangers and difficulties discussed in the introductory remarks here, at a scale likely to have a significant impact on the global energy balance, while further providing some added economic benefit so as to have a measurable incentive for implementation. Needed is a solution with a near-instantaneous effect that is readily measurable in direct physical terms, is rapidly deployable, and yet will dissipate or vanish of a timescale of one or more years following implementation, without further intervention. In short, as will be shown here, reflective forced cooling of the planet is a plausible answer to the problem of global warming and can be fitted into a business model with appropriate incentives. Devices, methods and means for achieving these ends are aspects of the invention as laid open herein.

Synergically, validated carbon sequestration is needed. As shown here, the inventive apparatus and methods realize convincing validation of carbon sequestration, and disclose a system for issuing validated carbon sequestration certificates that may be monetized or traded to finance continuing operations and incentivized to put a cost on continuing reliance on industrial, governmental and residential processes associated with greenhouse gas emissions. Validation of carbon credits or emission reductions is the essential component of any carbon trading market.

SUMMARY OF THE DISCLOSURE

It is clear that prior art efforts at fertilization of the sea have focused on high bioavailability—unnecessarily. A healthy neuston provides an excess of chelators, so exogenous EDTA or citrate is unnecessary. The prior art teaches against application of elemental iron because iron forms hydroxides that rapidly precipitate out of the photic zone. But must elemental iron necessarily precipitate from the photic zone? These tenants of the prior art, and others, are challenged here. The methods and compositions of the present invention are directed at simultaneously providing means for planetary cooling and means for increasing marine productivity through rational geoengineering.

Prior art efforts have sought to drive marine productivity by increasing the concentration of select essential elements, primarily iron, but have taken no notice of the effect of solid: water interface on partition coefficients, solubility constants, and biological activity. Merely increasing surface area in the ocean, absent any other effort, is sufficient to stimulate accumulation of biomass. The right combination of new surface area and increased nutrient supply, over an extended period of time, will result in superior performance of any biological system. More complex ecosystems are more stable and more productive over time. Complexity is both richness in trophic levels and in spatial niches, the fractal dimensions of Nature.

Described here are compositions, apparatus, and methods for biological and physical geoengineering. Disclosed are buoyant inorganic particles, prill, pucks, or floats having several properties: 1) a sustained-release composition for delivery of nutrients and minerals selected from iron, calcium, magnesium, zinc, copper, manganese, molybdenum, cobalt, chromium, nickel, vanadium, silicon, boron, cadmium, selenium, sulfur, inorganic nitrogen, and phosphate, resulting in increased biological productivity (ie. food), while synergically, 2) the compositions increase surface area for biochemical and photosynthetic activity in the neuston (ie. uptake of carbon dioxide), and 3) the compositions comprise a light-reflective skyward surface for cooling sea surface temperature when applied to bodies of water and are buoyant. These compositions are found to A) increase the potential for pelagic aquaculture, B) increase validated carbon sequestration and lithification, and C) provide some immediate relief from global warming by directly increasing planetary reflection and indirectly by increasing cloud nucleation activity. An installation in one location can influence albedo downwind in other segments of the atmosphere by kumogenesis. Preferred compositions are buoyant, essentially inorganic, and partially translucent. A preferred composition comprises a mixture of inorganic salts and binders (such as an inorganic glass) effective for increasing the growth of primary aquatic ecosystems such as coccolithophorids, diatoms, silicoflagellates, dinoflagellates, and microalgae (so-called "picoplankton") in a sustained-release composition having a $T_{0.5}$ of 0.5-3 years. Validation apparatus for assessing $CO_2$ sequestration are illustrated, and include vertical spar buoys designed to resist wave action while providing a stable long-term platform for "big science" oceanography—as docks for mooring of nutrient barges, supporting giant solar reflectors substituting for ice sheets, and supporting at depths a space frame with field of laser particle counters for measuring the $CO_2$ biological pump effect of sediment fall past the 100-Year Horizon, while not limited thereto.

These considerations have been unappreciated. In the dire situation in which we find ourselves, the goal must be not short term profit, but the long term productivity of the ocean at sustainable levels, with part of that productivity diverted to carbon sequestration. Therefore, it is appropriate to design and optimize sustained release compositions the half-life of which is measured in months or years, not days or even weeks. Such matrices are generally "stone-like" in nature— inorganic—and buoyant in water, an unlikely natural combination. But not impossible. There is added benefit by forming matrices having complex fractal surface topology at microscopic and macroscopic scales. In a preferred embodiment, the skyward facets of these compositions are reflective, thereby instantly modulating the albedo of the body of water upon which they are deployed.

In brief, the geoengineering devices and processes disclosed here combine biological and physical means for reducing global warming, increasing oceanic productivity, and are readily deployed on ocean surfaces. In one aspect, the invention is an inorganic, buoyant material for sustained release of a balanced mineral fertilizer. The fertilizer is balanced with trace and macro minerals and nutrients to support photoautotrophic growth where $CO_2$ is the principle source of carbon. By sustained release, a half-life $T_{0.5}$ of 0.5 to 3 years is contemplated. Mineraline compositions of the invention include compositions of iron, calcium, magnesium, and zinc with trace amounts of copper, molybdate, manganese, cobalt, chromium, borate, selenium, vanadium, and nickel, optionally supplemented with inorganic nitrogen such as nitrate, with phosphate, with sulfur or sulfates, and with blowgas enriched in $CO_2$, or other source of carbonates. Siliceous material is also a useful supplement for some target populations.

In another aspect, the invention is a reflective surface forming or formed of the skyward face of an inorganic, buoyant composition, the reflective surface causing an instantaneous increase in the albedo of a body of water. The compositions take the form of a prill, a puck, a pontoon, or a buoy, forms referred here generically as "sustained release compositions" (SRC).

In another aspect, the invention is a buoy or buoy array for scientific investigation of the effects of the above compositions on albedo and on carbon sequestration in an aquatic environment. The buoy floats with an extended vertical axis for stability independent of wave height and supports a surface platform for instrumentation and pumps for controlling depth. The buoy is associated with one or more rigid or semi-rigid rings which serve as booms, anchors for reflective rafts, and as part of a measuring apparatus for measuring particle sedimentation, a necessary part of any method to quantitate and validate $CO_2$ credits. In another aspect, the buoy is a platform for aquaculture. Elements of the platform are equipped with active buoyancy means and are submersible in the event of major storms or swells.

In another aspect, the invention is an apparatus for emitting a unit quantity of solar exsolation measurable in Joules from a terrestrial reflective surface to a plane above the upper terminus of the troposphere, wherein a solar exsolation credit instrument equal to the unit quantity of solar exsolation is produced and validated by the apparatus. Solar exsolation credits produced are optionally traded in a market or otherwise dispensed as credits against energy consumption, heat outputs associated with energy consumption, or greenhouse gas emission. A market for trading a solar exsolation credit will generally comprise a means for tracking and displaying an ask price and a bid price, and a means for executing trades such as are known in commodities markets. Other aspects of the invention will be apparent as discussed below.

In another aspect, the invention is an apparatus for validating sequestration of carbon below the 100 year horizon of an ocean and issuing a monetizable or tradeable certificate (CSCert) having a denomination based on the mass of carbon sequestered therebelow, which comprises: a) a spar buoy or network of spar buoys, each spar buoy with vertically elongate hollow body having a first end with superstructure and a second end with ballast mass, the hollow body having an upper fixed displacement volume V1 and a lower variable displacement volume V2; b) a horizontally disposed spaceframe suspended from the spar buoy or network of spar buoys at a depth at or below the 100 year horizon; c) an immersible analytical apparatus mounted on the spaceframe for measuring sedimentary deadfall data as an index of flux of sequestered carbon descending below the 100 year horizon of an ocean; d) a floating surface boom for enclosing a surface area of the ocean associated with the spar buoy or network of spar buoys; e) a composition dispersed within the enclosed surface area, the composition comprising an inorganic nutrient formulation in an inorganic, sustained-release matrix, the composition having a net aggregate positive buoyancy; and f) a computer-implemented system operatively connected to the analytical apparatus and configured for integrating flux of sequestered carbon descending below the 100 year horizon per unit time and issuing one or more monetizable or tradable certificates, wherein each certificate has a denomination equivalent to a validated amount of sequestered carbon as co2 in the sedimentary deadfall descended from the enclosed surface area to below the 100 year horizon.

Also claimed is any certificate (CSCert) produced by an apparatus or method disclosed herein, notwithstanding whether said certificate is found in the hands of a producer, a broker or an investor.

Also claimed is a data processing and communications system for registering or trading CSCert certificates in a market or through a broker, which comprises at least one server of a network, the server comprising one or more processors, at least one volatile memory, at least one non-volatile read-only memory containing instructions for the processor or processors, and having a dataport operably connected to at least one database, the database containing records, wherein the records include an inventory of certificates that have been registered and are available for trading and their denomination.

BRIEF DESCRIPTION OF THE FIGURES

The teachings of the present invention can be readily understood by considering the following detailed description in conjunction with the accompanying drawings, in which:

FIGS. 11A, 11B and 11C is a schematic of an extruder for forming SRC floats in a continuous ribbon-flow process.

FIG. 24 describes steps of a method for using an apparatus of the invention to issue a validated carbon sequestration certificate.

DETAILED DESCRIPTION

Figure 1:
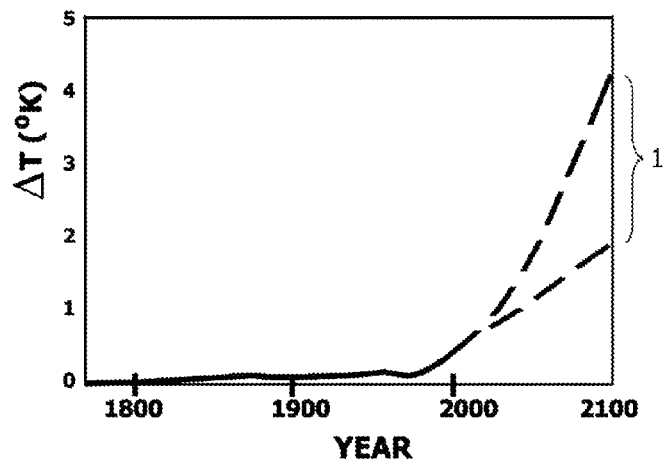
FIG. 1 is an extrapolation from best available models of global warming. The current range (1) of best estimates (IPCC: Climate Change 2007) for mean global temperature increase by 2100 is 1.8 to 4.0° C. The next report from the IPCC is due in 2014.

Although the following detailed description contains specific details for the purposes of explication, one of skill in the art will appreciate that many variations and alterations to the following details are within the scope of the invention. Accordingly, the exemplary embodiments of the invention described below are set forth without any loss of generality to, and without imposing limitations upon, the claimed invention.

Albedo—is the fraction or percent of reflected light from a surface as a ratio over the total incident illumination. Global albedo is the fraction of incident solar energy reflected from the Earth back into space. Albedo, in other words, is the ratio of exsolation to insolation, where exsolation is the quantity of reflected light exiting the atmosphere. A total energy balance for the planet reduces essentially to the energy of photonic insolation minus the sum of photonic and phononic out-radiation. As a matter of experimental convenience, meaningful insights into albedo can be made by comparing incident light and reflected light off a terrestrial surface. Since this incident light is largely depleted of wavelengths interacting with atmospheric species, visible reflected light is a significant component of global albedo. Several values for albedo are listed in the following table.

|  | Albedo |
| --- | --- |
| Snow and ice | 0.30-0.85 |
| Clouds | 0.35-0.75 |
| Desert | 0.25-0.30 |
| Forest | 0.05-0.15 |
| Open water | 0.05-0.08 |

Coefficient of reflection—the ratio of the total amount of radiation, typically visible light, reflected by a surface to the total amount of radiation incident on the surface. Preferably, reflective surfaces generally have a reflectance coefficient greater than 0.5. Some reflective surfaces are mirror-like. The reflective coefficient is measured by shining white light on a surface and measuring the ratio of reflected light to incident light.

Biocompatible—of a form that may be contacted with a food-chain in an aqueous environment without harm to number or diversity of trophic levels.

Net aggregate positive buoyancy—denotes a composition which displaces a volume of water having a weight greater than the weight of the composition. The composition typically contains a gas-filled void volume enclosed or dispersed in an inorganic matrix.

Mineraline—an inorganic form of an element selected from elemental, salt, oxide, hydride or hydrate, and generally confined to Groups I through VI of the periodic table, exempting lanthanides and actinides, and for the present purposes, typically limited to biocompatible elements selected from rows 2 through 6. Mineraline compositions are generally free of organic compositions. Mineraline compositions of the invention include compositions of iron, calcium, magnesium, and zinc with trace amounts of copper, molybdate, manganese, cobalt, borate, chromium, selenium, vanadium, and nickel, optionally supplemented with nitrate, phosphate, and with blowgas enriched in $CO_2$, or other source of carbonates. Siliceous material is also a useful supplement for some target populations and is a suitable inorganic binder.

Phosphorus supplementation is also contemplated, generally in the form of mineraline phosphates. Because the elemental composition of phytoplankton is generally C:N:P=106:16:1 (commonly referred to as the "Redfield Ratio"), about 100 units of carbon are delivered to the deep sea for every unit of phosphorus assimilated by phytoplankton in the photolayer and sedimented into the abysmal plains and trenches. This is the "biological pump" that delivers carbon from the atmosphere to the deep sea, where it is concentrated and sequestered for centuries.

100-Year Horizon—is a somewhat arbitrary functional boundary separating marine sediment-associated carbon that is recycled as part of the active food chain (and hence re-emerges as $CO_2$ by respiration) and carbon associated with sediments that are sequestered from the atmosphere for geological periods of time or ultimately remineralized. The 100-yr horizon is an accepted benchmark for validating carbon sequestration credits.

Carbon sequestration certificate: generally refers to a certificate comprising a $CO_2$ sequestration certificate, a $CO_2$ emission permit, a $CO_2$ emission credit, a carbon offset, a carbon allowance, a criteria pollutant allowance, a Verified Emissions Reductions unit (VER), a Carbon Financial Instrument (CFI), a European Union Allowance (EUA), a Certified Emission Reduction unit (CER), an Emission Reduction Unit (ERU), or a Voluntary Carbon Unit. Carbon sequestration certificates (CSCerts) are denominated in moles or mass of carbon, either as atomic carbon or as carbon dioxide equivalent carbon.

SRC—refers to "sustained release composition", that is, inorganic mineraline formulations in the form of a granule, pellet, puck, prill, microsphere, pontoon, sheet, plate, or agglomerate having a positive buoyancy. The compositions release physiologically acceptable concentrations and forms of elements required for photosynthesis with sustained release kinetics. The shell, the core, or the matrix of the solid member typically contains a gas phase. SRC with porosity or a fractal roughness are also provided. A buoyant core may be coated with a sustained release layer. Optionally, these formulations are light-reflective or are prepared with a reflective surface. In a preferred composition, the formulation floats with a reflective surface oriented skyward.

Cenospheres, vermiculite (exploded mica) and composites of vermiculite or perlite and kaolin, talc, pumice, exploded clays, zeolites generally, scoria, $CaCO_3$, or glass, as well as artificial foamed silicates made from hydrosols are other potential inorganic substrates for SRCs. One type of cementitious, spray-foam insulation is known as Air-Krete™. It contains magnesium silicate, has an initial consistency similar to shaving cream, and is fireproof. For many years, hollow glass microspheres have been available in quantity and may be used to impart buoyancy to inorganic formulations made with an inorganic binder. Unlike ordinary glass microspheres, retro-reflective glass microspheres are well known for their use in bright reflective surfaces. Such microspheres have refractive indexes in the range of 1 to 3 and are suitable reflectors even when immersed in water. Glass microspheres may be coated with a variety of metallic reflectors. Ceramic and metal hollow microspheres are also commercially available. Manufacture of hollow microspheres is readily accomplished, taking advantage of the interfacial tension of a gas in glass collet, and a process equivalent to Ostwald ripening at temperatures at which the substrate is plastic. Formulations made of foamed clays are also provided.

Float—refers to a pontoon, raft, barge, boom or other displacing structure that is larger than a prill or a puck. Also comprises pontoon structures and combinations thereof. Floats may be individually dispersed or tethered.

Trophic levels—refers to one or more pools of carbon in a food chain. Typically a "primary producer level" or levels occupies the base of the food chain. Direct grazers occupy a second level. Larger predators occupy a third level, and so forth. Over the past 25 years our vision of the pelagic food web structure has changed dramatically. We now view the traditional "diatom-copepod-fish" foodweb as a relatively minor component. The food web consistently present in all oceanic habitats is based on pico- and nanoplankton-sized autotrophs and heterotrophs, which are efficiently grazed by flagellates and ciliates. The pelagic food web is microbe-centric. ("Microbe" in this context means small autotrophs, heterotrophs, and mixotrophs, and refers to both prokaryotes and eukaryotes.) A necessary effort in carbon sequestration is an effort to shift the food web to include higher trophic levels. The principal means for doing this is by supplying habitat and solid phase surface area, not merely iron.

Turning now to the figures, FIG. 1 is a representation of future global temperatures given current trendlines. Shown are high and low "best estimates" prepared by the IPCC.

Figure 2:
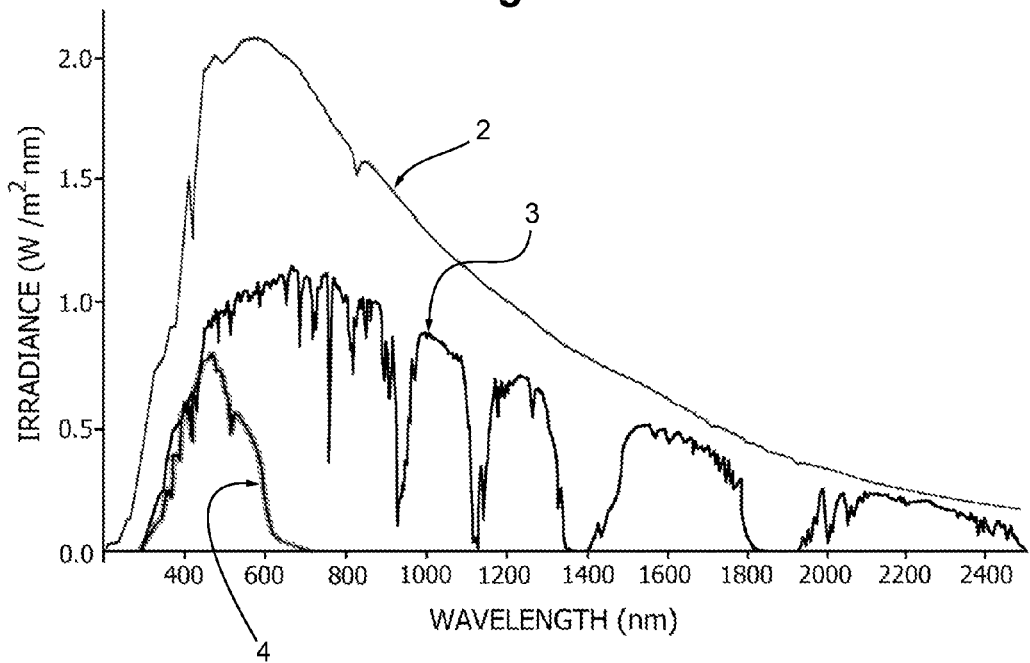
FIG. 2 is an adaptation of a spectrogram of solar radiation as received at the top of the atmosphere (2), at the surface at sea level (3), and at a depth of 10 meters below an ocean surface (4), for wavelengths from the UV to the far infrared.

FIG. 2 shows a spectrogram of incident solar irradiation as a function of wavelength and altitude, the upper curve showing solar energy ($W/m^2$-nm) entering the atmosphere (2), the middle curve light energy striking the surface of the ocean (3), and the bottommost curve (4) light having been depleted after penetration to a depth of 10 m below the ocean surface. The area under curve 3 and above curve 4 is the light energy converted to heat in the top 10 m of ocean. Clearly all light entering a deep body of water is fully absorbed. The oceans, covering more than half the surface of the globe, are thus major engines of climate. Reducing this heat engine is a rapid and effective way to force global cooling.

Figure 3:
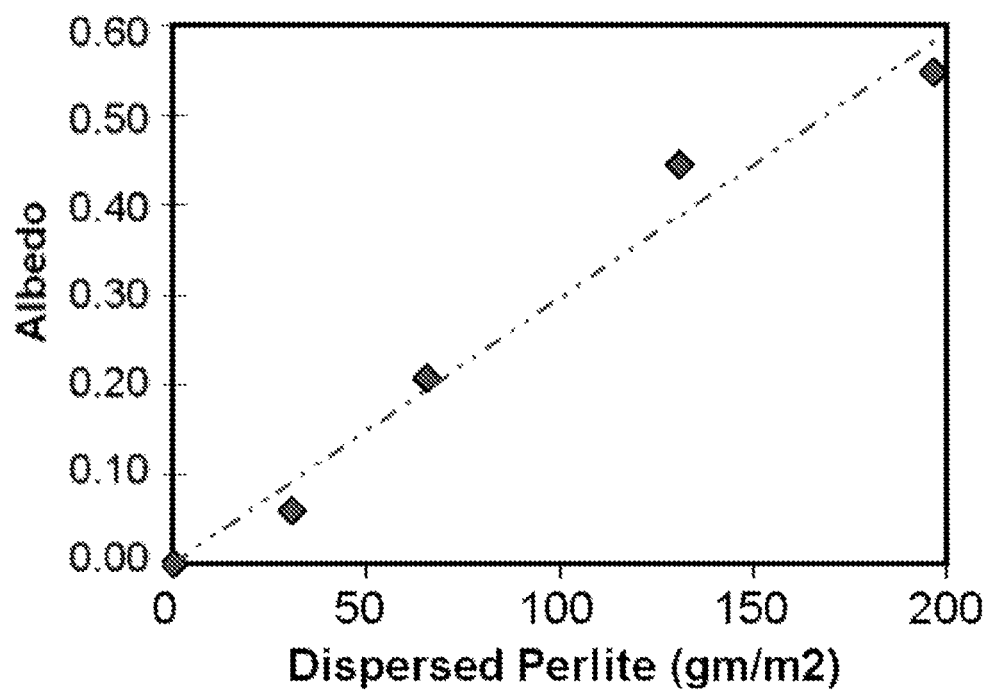
FIG. 3 is an experimental result, shown relative density of perlite as reflector on water and the corresponding albedo measured with a solar collector and using incident radiation as a denominator.

FIG. 3 is a plot of data from an experiment in which prill (perlite, horticultural grade) is weighted out and dispersed on a defined surface area in a dark-bottomed tank filled with water. This material contains a significant proportion of fines that contribute poorly to reflectivity. Perlite is a snow white material manufactured by "exploding" a porous, moist mineral found in deposits associated with volcanic ash and pumice. For the experiment, incident radiation was measured amperometrically with a solar panel and conditions were selected where the current response was generally linear. The effect of increasing quantity of reflective prill was then tested by turning the solar panel upside down over the tank (with incident light at about a 30 degree angle) and measuring the reflected light in the same way. A zero-intercept was obtained experimentally when no prill was added to the tank. A fill factor can be estimated from photographs taken during the experiment (such as FIG. 4). Even at 30 $gm/m^2$, increases in albedo of the order of +0.05 were obtained. This is a highly significant change in energy flux if taken over a very large surface area.

Albedo at high fill factors of floating perlite on water approaches 0.6. By comparison, the albedo of snow is typically reported as 0.3-0.85, depending on the cleanness of the snow.

Figure 4:
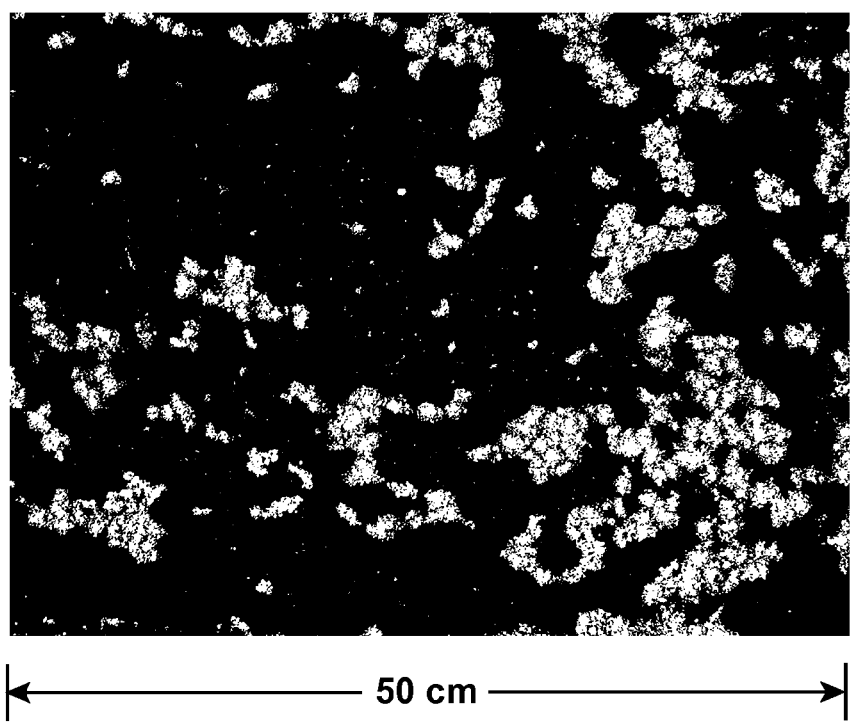
FIG. 4 is a view of a water-filled experimental tank containing 30 gm/m² perlite dispersed and floating on the surface.

FIG. 4 is a b/w reproduction of a photograph of an experimental setup as described above, although the sun was slightly higher in the sky. A fill factor of 30 $gm/m^2$ perlite is shown. Some clumping of the perlite is observed.

Figure 5:
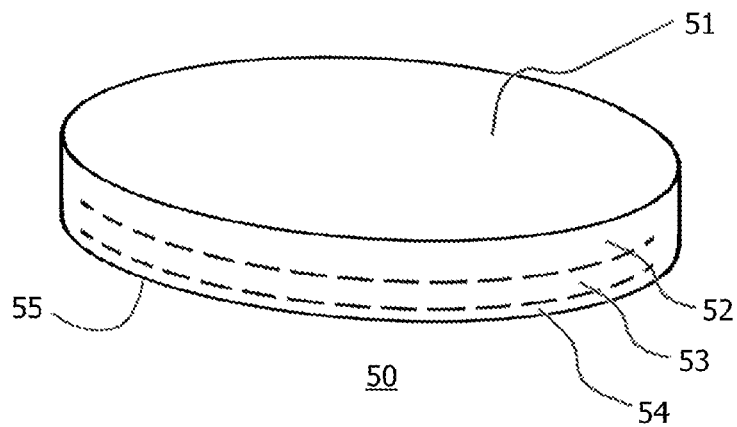
FIG. 5 is a sketch of a composite SRC in the form of a puck.

Fill factor is rarely so high that gas exchange is inhibited. Moreover, by use of translucent prill or pucks, aerobic photosynthesis will supplement aeration in the water below the floats. Preferably oxygenation occurs by a combination of gas exchange and photosynthesis, and provides sufficient oxygen to support complex multilevel trophic layers including predators. Where floats are dispersed but are vertically elongate in the water column, they may function like underwater forests of macro cystis pyrifera, which have high productivity despite diminution of light as a function of depth and a typical thatch of fronds on the water surface that would be expected to slow gas exchange. In short, the floats are expected to support living elements that function as the ecological equivalent of the community's lungs and do not result in anoxia FIG. 5 is a schematic view of a puck (50) formed with multiple layers. The upper surface (51) is a reflective surface and for example is comprised of titanium oxide, silicon oxide, zirconium oxide, or glass, and may contain platelets of mica or metal or crystals of olivine, or other reflective material such as a thin mirror layer of aluminum. The upper layer (52) is rich in low density materials for positive buoyancy and is optionally comprised of perlite in an inorganic binder of waterglass or exploded porcelain, for example. The middle layer (53) includes a slow release matrix and contains mineraline inorganic nutrients selected from iron, calcium, magnesium, zinc, copper, molybdate, manganese, cobalt, borate, selenium, vanadium, and nickel, optionally supplemented with nitrate and phosphate. The minerals are supplied as oxides, nitrates, carbonates, silicates, sulfates, or as elements. The redox state of the minerals is selected for cost and convenience in formulation because bioavailable redox species are formed in situ. The matrix is formulated so that the elements are released in biologically nutritive quantities over an extended period of time, preferably the matrix dissolves with a half-life of 0.5 to 3 years. This middle layer is formulated with a higher density, as ballast, so that the puck will float with the upper layer facing skyward. A lower layer (54) may be added for quick release, and also serves to reduce fouling by virtue of its higher erodibility. The net buoyancy of the puck is positive. A porous coat (55) such as a leachable glass may also be added to improve handling during transport and dispersal.

Various methods known in the art may used to make porous sustained release materials from ceramics. The polymeric-sponge method produces open-cell structures by impregnating a polymeric sponge with a ceramic powder slurry, the organics are then driven off at a temperature below that required for firing the ceramic slurry material. Polymers sponges include polyurethane, cellulose, polyvinyl chloride, polystyrene, and latex. Alternatively, a direct foaming method can be used to produce both open-cell and closed-cell structures. In this method, a chemical mixture containing the desired ceramic component and gas precursors is treated to evolve a gas. Bubbles in the material cause it to foam. The resulting porous ceramic material is then dried and fired. Honeycomb structures may also be made. Firing the green ceramic typically involves a temperature of 1000-1700° C., however, improvements have been made that significantly reduce the firing temperature as described in U.S. Pat. No. 7,169,725 to Haun, and adaptations thereof. Porous ceramics can also be made by freeze drying a precursor followed by sintering (see for example: Deville, S. 2008. Freeze-casting of porous ceramics. Adv Engin Matls 10:155-169), and adaptations thereof. Sol gel and water glass methods may also be use.

Figure 6:
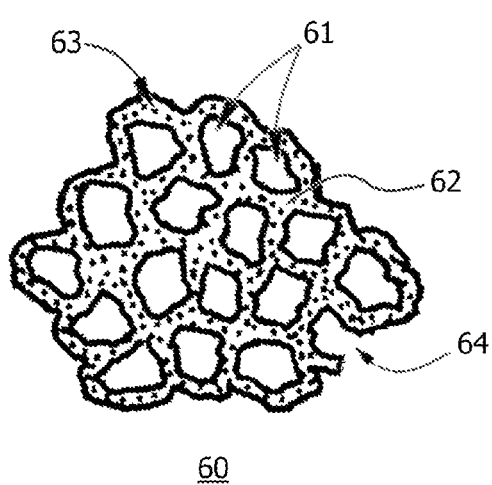
FIG. 6 is a section through a composite SRC granule or prill.

FIG. 6 is a cartoon showing a section through an amorphous SRC granule or prill (60). Voids (61) filled with gas are used to reduce the aggregate density, because the particle must float. A glass or ceramic matrix (62) material is used to bind mineraline elements (63) into a solid granule. Voids (64) on the surface of the particle increase surface area, promote surface chemistry, and facilitate colonization with microorganisms that will erode the matrix over multiple months or even years. The matrix material is a clay or a glass, for example a silica glass or kaolin, while not limited thereto. The granules (60) are preferably white or are optionally coated with embedded specular reflectors such as glass microspheres or quartz or mica platelets. The granules or pellets may contain a single void. Glass floats used in the early part of this century by Japanese fishermen have been known ride the Kuroshio current north, circling the Pacific for decades and in fact still wash up on Oregon and Hawaii beaches after storms. The spherical floats vary in size from a few centimeters to almost a meter in diameter, and even accumulate barnacles, eventually sinking under the accumulated weight.

Preferably the composite material is translucent or partially transparent so that sunlight that is not reflected can penetrate a few meters into the ocean and result in photosynthetic activity. The percentage of reflective cover, translucent cover, and openings between the granules is adjusted to ensure that primary productivity is strongly photoautotrophic. Activation of photosystem II ensures that the water in top meter is strongly oxygenated.

Figure 7:
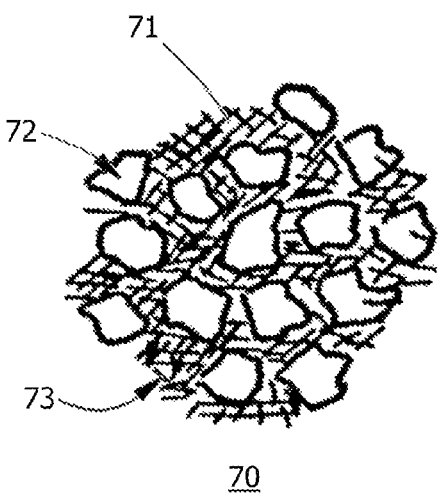
FIG. 7 is a section through a composite SRC granule with fibrous matrix.

FIG. 7 is a cartoon shown a section through an amorphous SRC pellet (70) with a fibrous low-density matrix (71). Granules (72) of a slow release material and fibers (73) are embedded in the matrix (73). Non-wetting voids in the matrix hold air sufficient for buoyancy. The matrix is typically a ceramic or a glass.

Figure 8A:
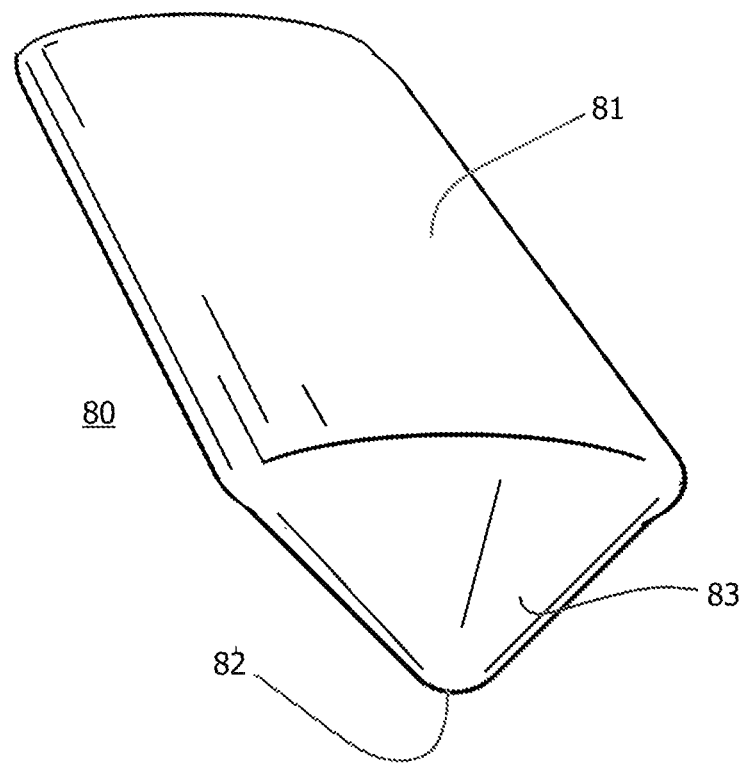
FIG. 8A is a perspective view of an extruded float and FIG. 8B is a cross-section of the float showing multiple layers.
Figure 8B:
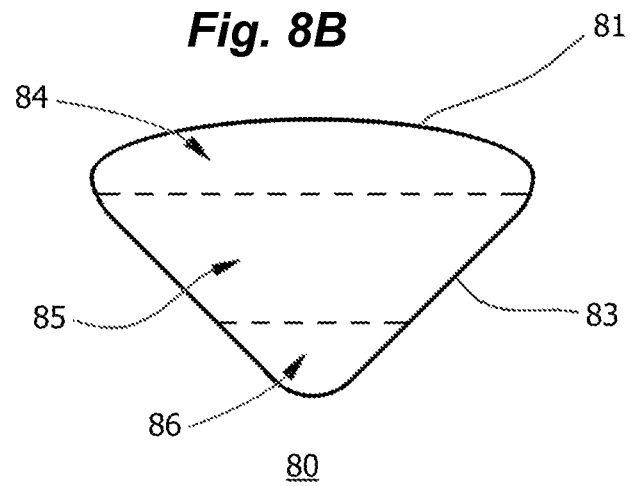

FIGS. 8A and 8B show an extruded product (80). This float is manufactured by cutting a ribbon of extruded matrix material into convenient lengths. Each float comprises a reflective cap (81), a ballasted keel (82), and a glass coating (83).

FIG. 8B illustrates a section through a float of FIG. 8A. The float is comprised of three layers, an upper buoyant layer (84) with entrapped air, a middle layer (85) with mineraline elements formulated in a slow release matrix of neutral density, and a lower layer (86) with embedded iron filings and serving as a ballasted keel. The floats are spray coated with water glass or hard coat and sintered during manufacture.

Figure 9:
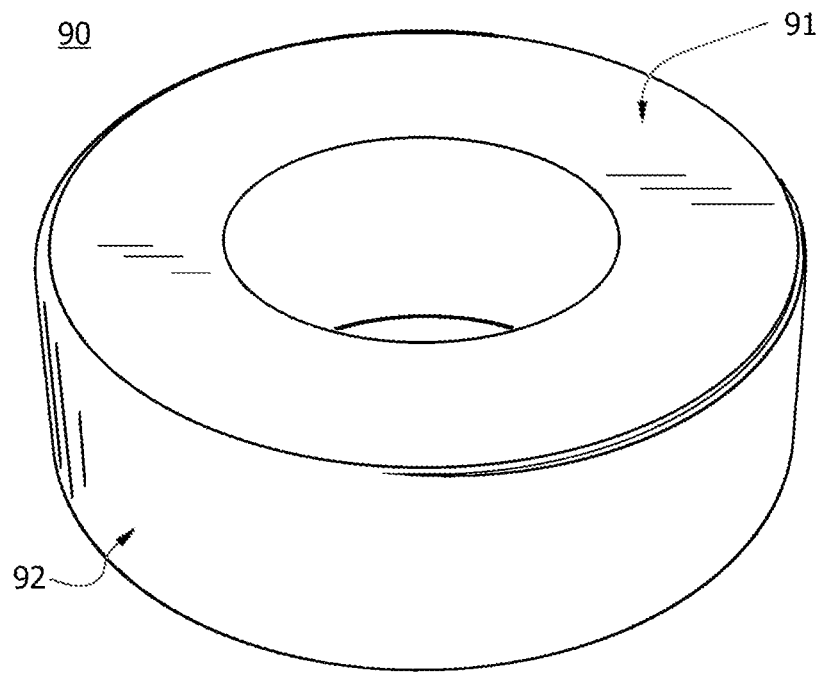
FIG. 9 is a sketch of a toroid puck with sustained release matrix and reflective cap.

FIG. 9 shows a toroid float (90) having a net positive buoyancy, a sustained release core, and a hard coat outer layer (92), the cap (91) with reflective properties. Floats may optionally be tethered together to form a net-like sheet when dispersed.

Figure 10:
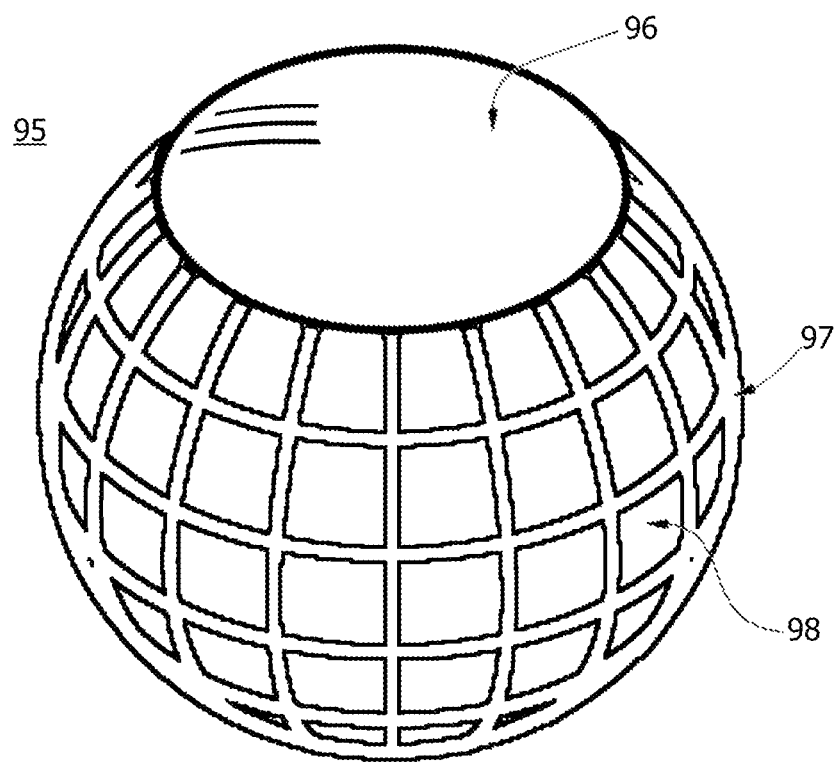
FIG. 10 is a sketch of a hollow ribbed spheroid float with buoyant cap.

FIG. 10 shows a hollow ribbed ball with a reflective cap (96) having a core of low density matrix material and erodible ribs (97) having a mineral composition for sustained release. The ribs are strengthened to resist breakage. Apertures (98) between the ribs permit the entry of organisms. The ball may be provided with pendant flexible stringers that hang vertically below the ball when floated and provide additional nursery space and complexity of niche levels for multilevel higher trophic communities as favors production of macroscale fecal pellets having a higher sedimentation rate. By spacing the balls, for example by suspending them from a overhanging trellis, columns of sunlight are permitted to enter the water between the balls so that light penetrates 10 meters or so between the pendant stringers, a sort of upside down forest for maximizing productivity.

FIGS. 11A, 11B and 11C are illustrative of an extruder process nozzle used to manufacture the float of FIG. 8. Extruded product is indicated by V. Four feeds are fed into a triple nozzle (101) with outer sheath (110) that is inserted into an alcohol bath (111) through process tank wall (102). Feed III is the iron rich bottom layer in a clay matrix and is fed in at (103). Feed IV is a gas bubble rich upper layer of waterglass as a slurry rich in specular reflective material such as titanium oxide or mica platelets and is fed in at 104. Feed II is a core layer of slow-release mineraline elements important for photosynthesis in a waterglass slurry and enters through a nested tube (105). Feed I, entering the core of the extruded ribbon at 106, is an alcohol that solidifies the waterglass matrix and is removed and recovered during sintering under a $CO_2$ atmosphere. The product is characterized by high porosity and voidspace.

Figure 12A:
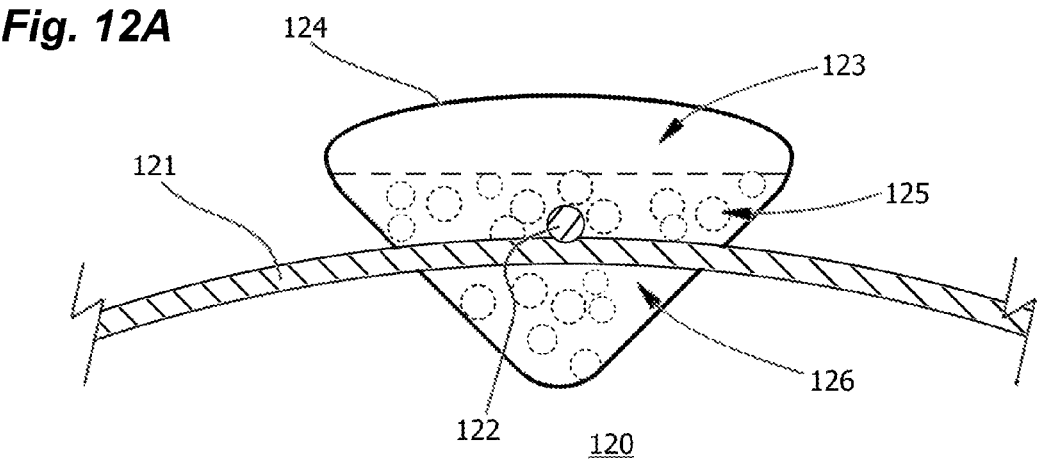
FIG. 12A is a sectional view of a float in which a hoop has been embedded.

FIG. 12A is a modified float (120), here shown in section to illustrate that a barrel hoop (121) and stave (122) has been embedded in the float. Again the reflective cap (123) is present and may be a coating. The upper layer (124) is buoyant. Under the upper layer is a body comprised of granules of mixed metal oxides (125) and a slow release clay matrix (126).

Figure 12B:
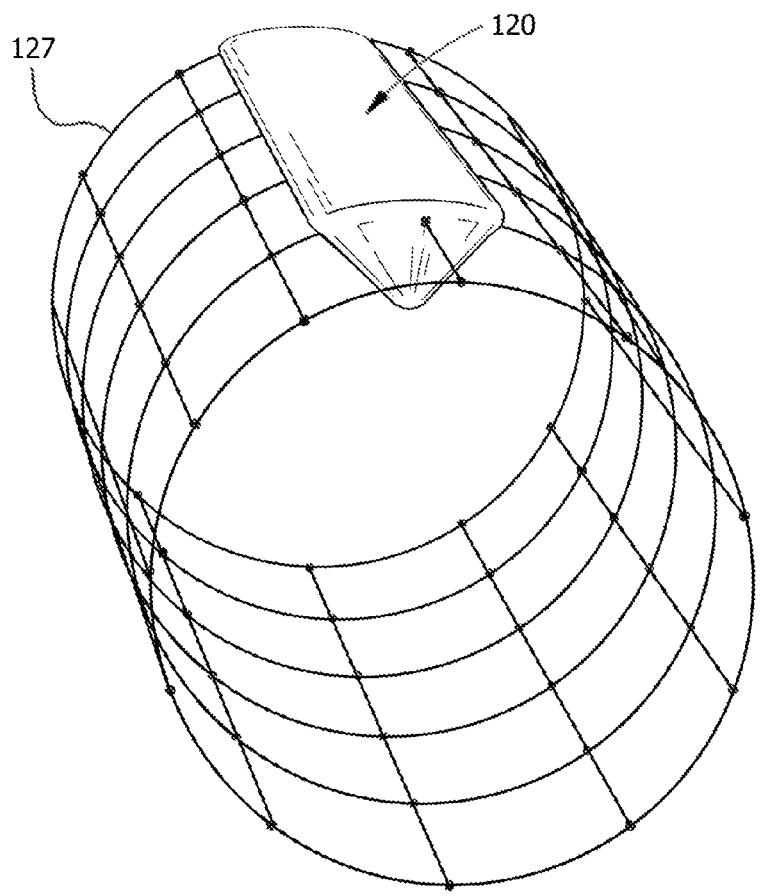
FIG. 12B is a perspective view of the float of FIG. 12A.

This complex float is rendered as a complete structural unit in FIG. 12B. Here the float (120) is shown with embedded wire barrel (127), the wire barrel forming habitat for larger trophic levels, and a sort of pelagic nursery. The wire barrel also serves to prevent the floats from closing together in impenetrable poly-rafts that would block light penetration or gas exchange. The float may be a meter or more in length if desired.

As shown in FIGS. 5-12, the invention is a buoyant composition for sequestering fixed carbon below the 100-Year Horizon of an ocean, for increasing marine biological productivity, and with reflective for increasing the albedo of a body of water. The composition comprises an inorganic nutrient or nutrients, generally in a formulation with balanced physiological ratio for supporting primary production of one or more food webs, in a sustained release solid matrix, the solid matrix having a light reflective surface or surfaces for cooling the sea, as heat can reduce biological productivity.

Figure 13A:
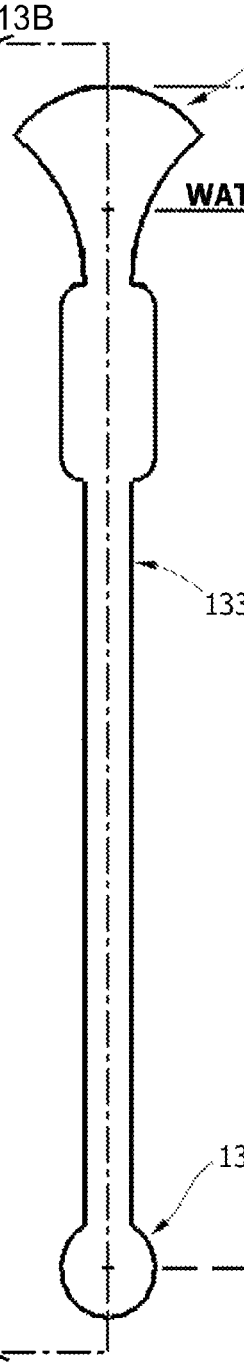
FIG. 13A is a half-section or outline view of a hollow, columnar buoy for marine field work on carbon sequestration and/or ocean albedo.

Turning to FIG. 13A, shown is a vertical spar buoy (130) configured to float with about 90% of its mass submerged relative to the waterline. The buoy comprises a hollow, elongate vertical body with superstructure (131) and ballast (132) assembly at the two ends joined in the middle by an elongate stem (133). The submerged understructure is a hollow tube with horizontal partitions in the upper levels and can be filled like a straw up to those partitions. The partitions separate an upper fixed displacement volume V1 and a lower variable displacement volume V2. Pumps are used to regulate the waterline, which is dynamically controllable. A self-propelled vessel that could be partially flooded at one end to assume this vertical posture was tested by Scripps Institute of Oceanography and found to provide a remarkably stable platform for oceanographic research that resisted pitch and yaw. Here the principle is adapted as a passive buoy for semi-permanent mooring on an anchored cable, and as will be shown below, combinations are introduced that build on this platform.

Figure 13B:
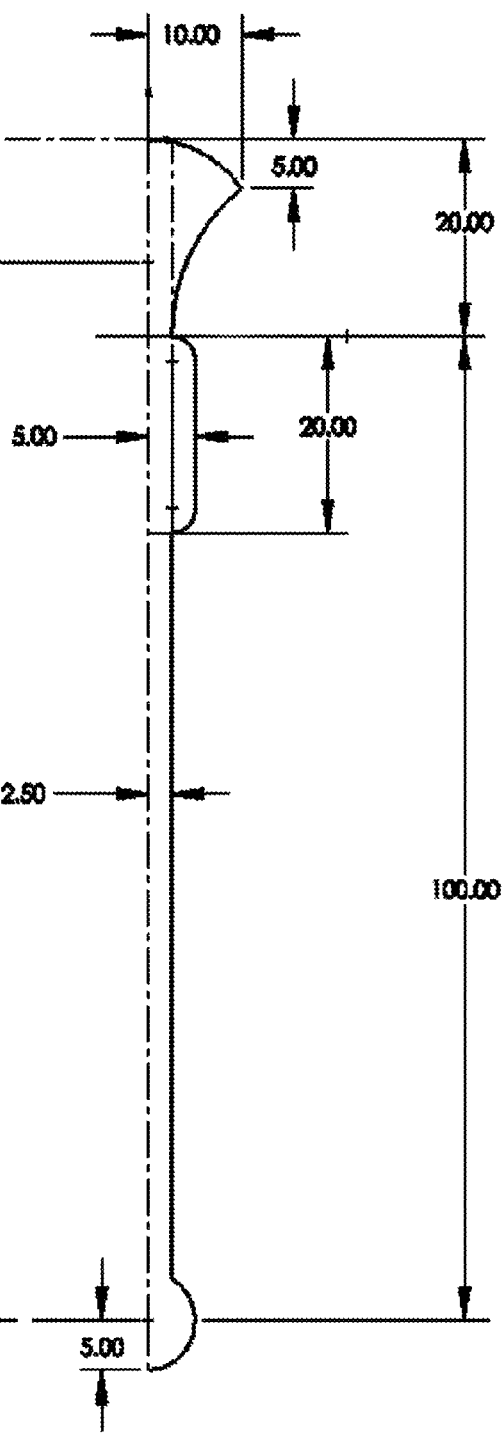
FIG. 13B indicates approximate dimensions of a buoy designed to float with a waterline as shown.

FIG. 13B provides dimensions (in meters) for a structure of this class. Tubular construction with ferrocement, geocement, welded aluminum, or fiber-reinforced PVC forming the stem is contemplated, for example on a removable mandrel, from pre-shaped sections, or by shotcrete construction in a female mold using a track-mounted blower. In this model of the buoy, the total mass was $3.6 \times 10^6$ kg (assuming ferrocement), the displacement was $5.6 \times 10^6$ cubic meters of seawater, and the ballast mass on the bottom of the stem was $1.7 \times 10^6$ kg. This yielded a waterline about 17 meters from the top of the superstructure. The stem is partially flooded and the actual water line is controllable by controlling the level of water within the stem.

By use of internal structural partitions, a minimum waterline can be maintained. The structure is submersible. Submersion at a depth of 20 meters has an important advantage in weathering severe storms. The buoy may be anchored. The entire structure may be pulled down 20 meters under the ocean on a cable to ride out storm surges.

Figure 14:
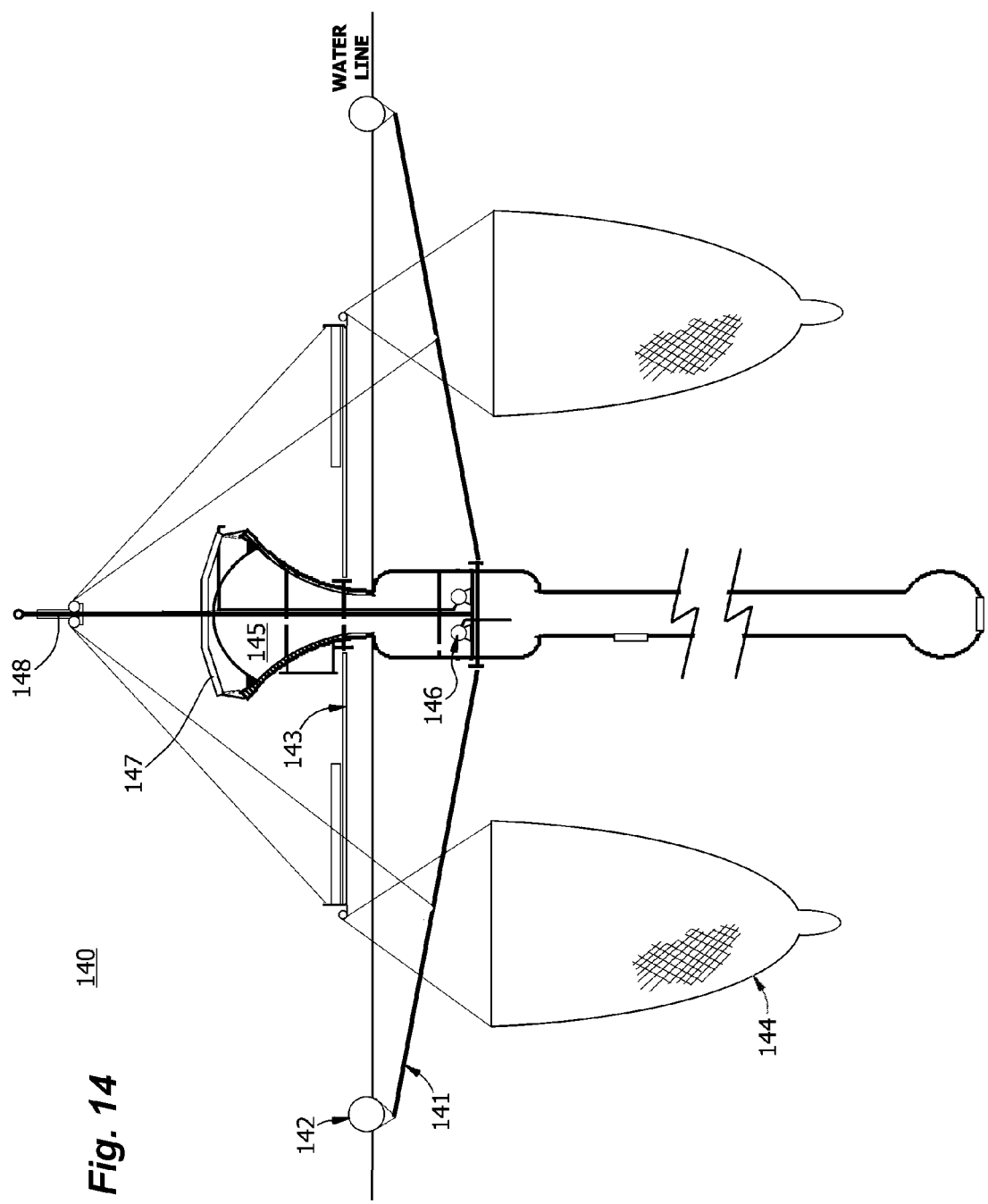
FIG. 14 is a cartoon showing a columnar buoy with outriggers for anchoring a tubular boom used to retain SRC in a test zone and nets to capture detritus from the associated bloom.

FIG. 14 depicts a more complex buoy combination (140) on which a research platform is built. Outriggers (141) are used to anchor a tubular barrier float boom (142) or ring-like pontoon around a defined surface area of water. SRC are dispersed within the encircling float boom. The outriggers are collapsible and can be drawn up during storms. Gantryways (143) give access out to suspended nets (144) where samples can be taken. A laboratory (145) for sample processing and measurement is provided on an upper deck, with access to a pump room (146). The pumps are used to control the level of the waterline. An upper observation deck or solar panel installation (147) is mounted above the superstructure along with egress to the gantryways. An antenna (148) is mounted so that data may be streamed to satellite transceivers during automated operation.

Structures of this sort have a positive effect on local marine productivity. It is known that fish associate with floating objects (Hunter J R and C T Mitchell. 1966. Association of fishes with flotsam in the offshore waters of Central America. Fishery Bulletin 66:13-29); however, increases in primary productivity are greater than can be accounted for by clustering of schooling fish around buoys. SRC within the pontoon corral or "boom" result in a sustained bioavailability of trace minerals for primary producers and habitat and surface area for higher trophic levels without use of exogenous chelators. Sustained concentrations of iron(III) in the nM range, for example, exceed the $K_{sp}$ for iron in seawater—due to natural organic chelators released by organisms (see for example Kuma K et al. 1996. Controls on iron(III) hydroxide solubility in seawater: the influence of pH and natural organic chelators. Limn Oceano 41:396-407; Morel F M M and N M Price. 2003. The biogeochemical cycles of trace metals in the oceans. Science 300:944-47). Because biouptake controls the equilibrium between solubilized iron and the solid phase compositions, even elemental iron may be used as a source of iron in the SCR. Growth of biomass does not result in other elemental deficiencies secondary to consumption of iron because the formulations are typically supplemented with a full range of minerals in a balanced composition. Sustainable yields of a higher trophic level from the sea surrounding the installation are expected to rise.

Figure 15:
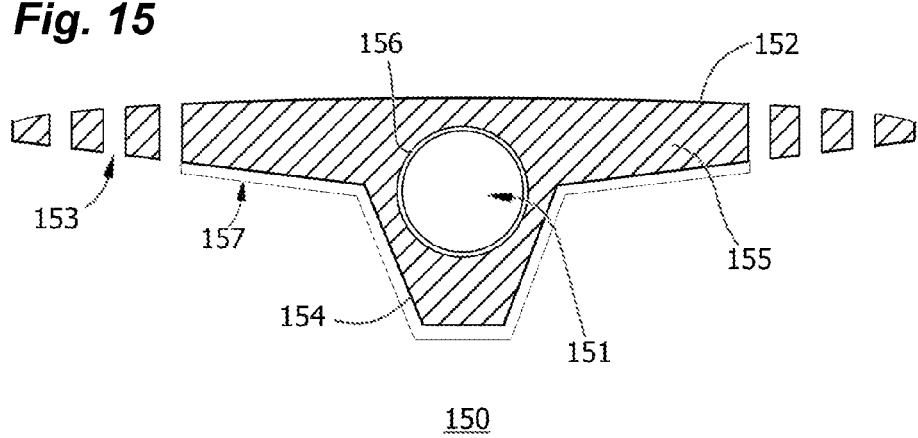
FIG. 15 shows an SRC formed as a large pontoon with reflective deck and keel piece.

FIG. 15 shows an SRC of several meters in width. This is a section through the structure of the pontoon; which is part of a larger structure forming a boom around a centrally anchored research platform. The boom may have a degree of flexibility while being relatively incompressible in diameter. In the center of the pontoon (150) is a hollow tube (156) that is filled with air (151) during surface operation. The top of the pontoon is a reflective surface (152) or coating, which may be periodically cleaned. The pontoon is perforated (153) to promote aeration during wave surge. A keel (154) is used for ballast. The core (155) is preferably a neutral density material. The rings are flexible so that the ring can undulate during passage of a swell. Optionally, an erodable anti-fouling coating (157) is supplied that contains an inorganic nutrient mix for supporting the growth of photosynthetic organisms. Erodable anti-fouling coatings need not be buoyant when applied to a floating pontoon or structure.

Figure 16:
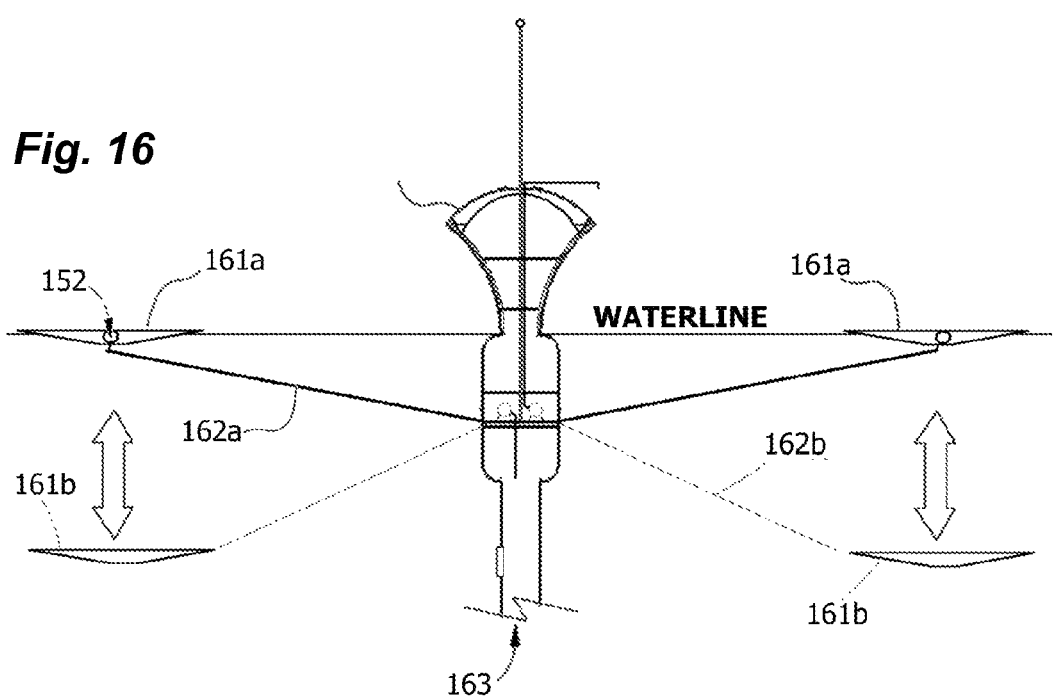
FIG. 16 shows a columnar buoy with outriggers in two positions, first (solid line) with SRC pontoon boom afloat and second with SRC pontoons flooded for submergence during storms.

FIG. 16 demonstrates how the rig may be weatherproofed during a storm. The ring-like boom (161a, surface position) floats during regular operation, serving as reflector with mirror upper surface and as a retaining barrier for confining a study area. Suspension cables (162a, surface position) like the spokes of a wheel ensure that the ring is held off from the buoy. But when the internal tube (151) of the ring is flooded through the stem (163), the boom (161b, submerged position) sinks below the surface of the water (arrows), as would be prudent when ocean swells increase above a critical threshold. The cables (162b, submerged position) again are in tension to prevent the boom from sinking The cables may have an elasticity in order that wear on rigid fittings is minimized, but rigid cables are also useable. Because tensile loads are distributed by multiple cables onto a reinforced ring of the buoy hull, little danger of simultaneous catastrophic failure exists. Alternately, the central spar may also be submerged as when winched down on a cable connected to a seafloor anchor but while retaining positive buoyancy.

Figure 17:
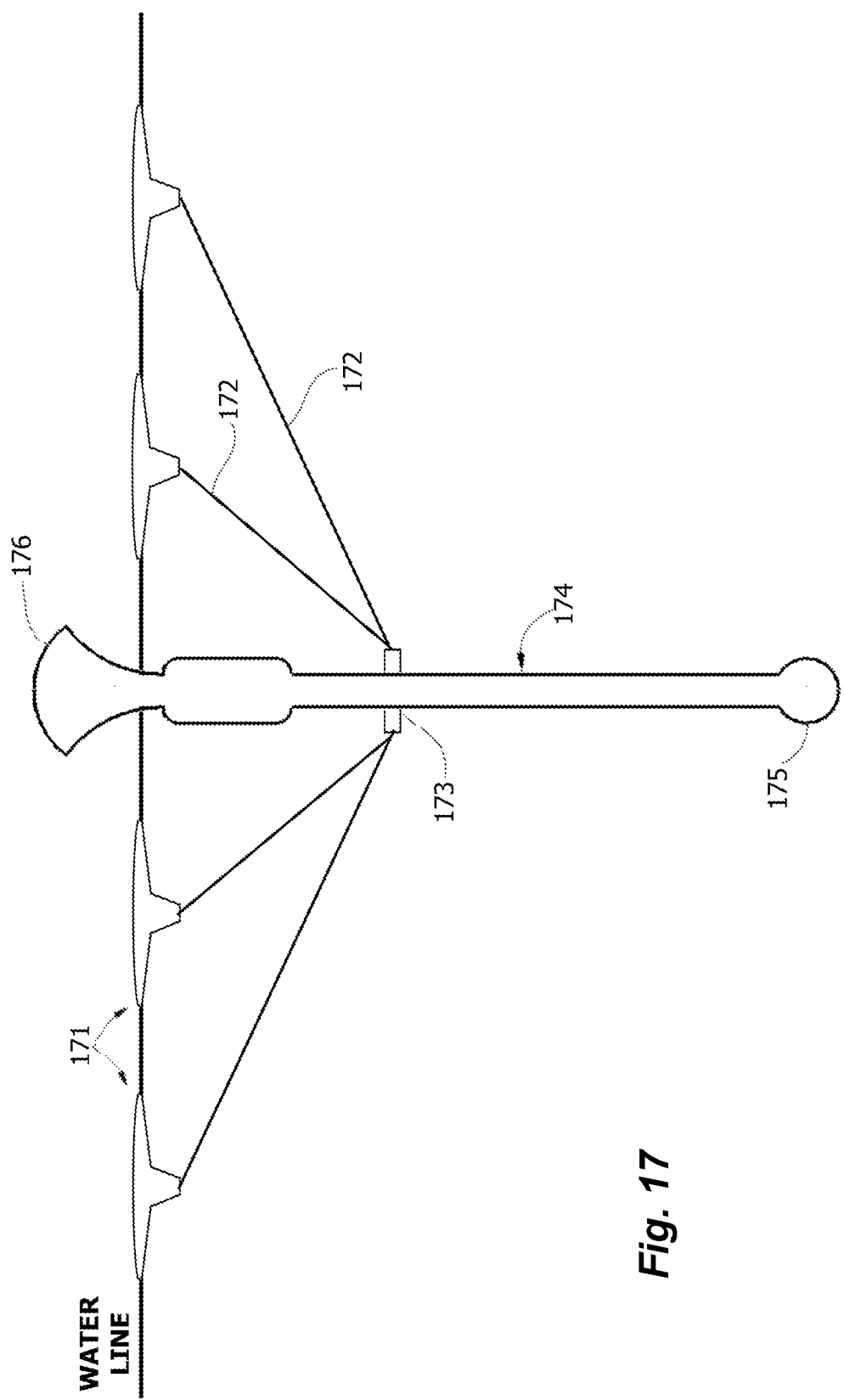
FIG. 17 shows a buoy with nested circular pontoon booms.

FIG. 17 is a schematic of a single buoy with multiple boom platforms (171) at different diameters, held in place by nested cables (172). This form can be used to increase the reflective surface of the installation, and provides a large floating platform for pelagic aquaculture or research on carbon sequestration. In one embodiment, by mobilizing the collar yoke (173) on the central stem (174), fluctuations in the level of the outside rings do not result in excessive strains on the cable supports. Ballast (175) dampens oscillations of the buoy that would otherwise be associated with rough seas, so that the superstructure (176) remains level during transient fluctuations of the waterline.

Figure 18:
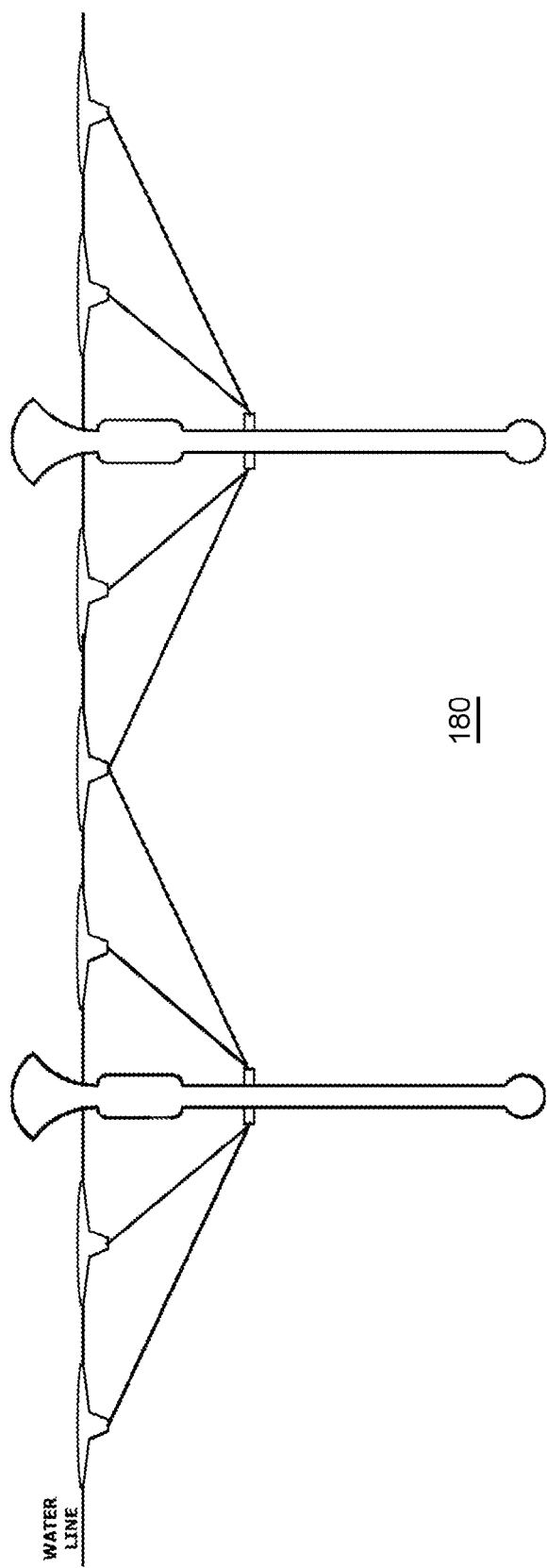
FIG. 18 shows a buoy network interconnected by cables at the outer pontoons, forming by extension a hexagonal planar array of booms and buoys.

FIG. 18 shows how the buoy platforms can be merged into planar arrays (180). By using large arrays, island-sized floating platforms can be constructed. This feature permits phased deployment of the pelagic reflective nutrient arrays of the invention while monitoring for adverse effects as scale is increased.

Figure 19:
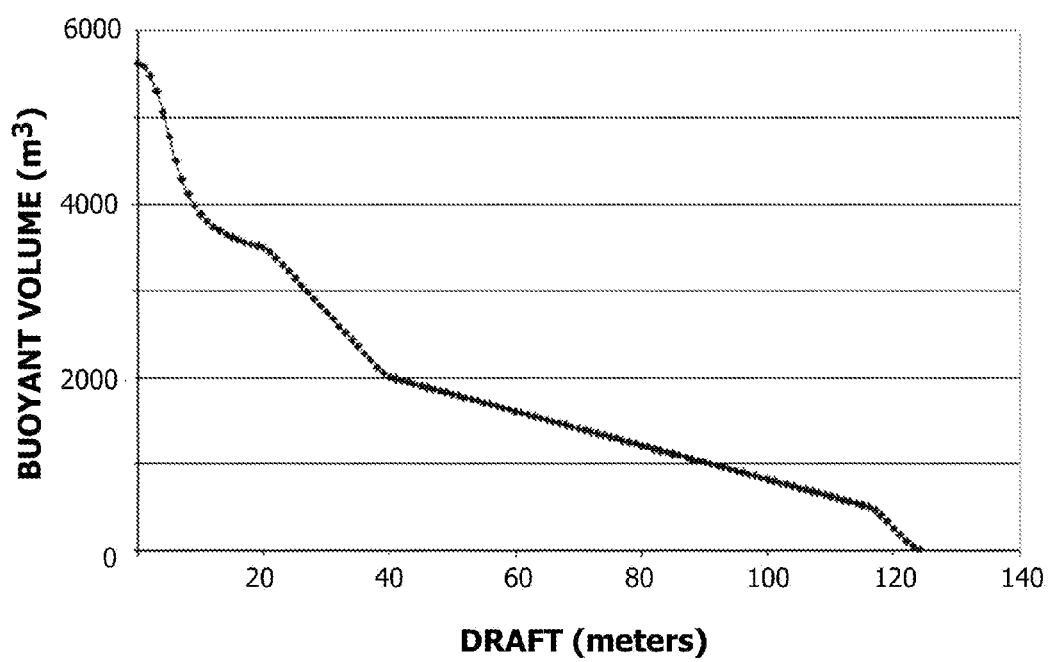
FIG. 19 is a graph of buoyant volume (displacement in $m^3$) versus depth or draft on the structure.

FIG. 19 is a plot of calculated displacement volume versus depth mark (draft) on a plimsoll. As would be expected, displacement volume increases from the ballast segment at the bottom of the structure (the 120 meter mark) and becomes maximal as the superstructure exits the waterline. The waterline is dynamic but is typically placed at the 20 m mark. Cumulative total displacement at the 20 m mark is about 5600 metric tons as required for a heavy ferrocement structure. Lighter displacement designs using alternate materials are also feasible. Inertial forces causing the structure to sway laterally and to rise and fall in the surf are heavily dampened by the masses involved and the low overall center of buoyancy.

Figure 20:
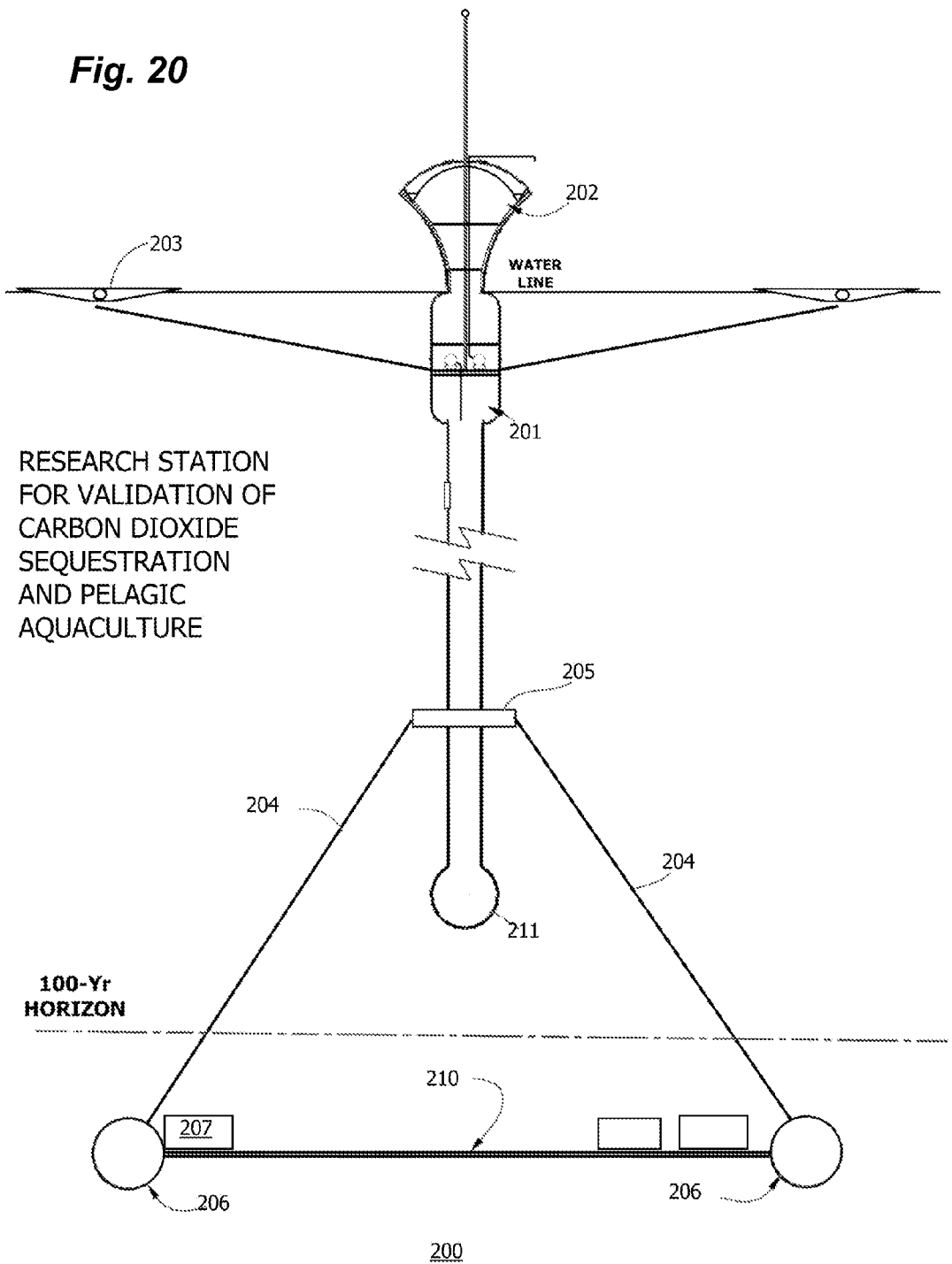
FIG. 20 is an integrated view of a research station, with floating pontoon booms as part of an aquaculture/marine fertilization facility and with a spaceframe and instrument package suspended by cables at or below the 100 Yr-horizon for validating carbon sequestration by measuring sediment deadfall mass along a transect or over a sampling area.

FIG. 20 shows in schematic an integrated oceanographic workstation (200) with central spar buoy (201) with superstructure (202), ballast (211), and surrounding float boom (203) supporting, on suspended cables (204) from an adjustable yoke (205), a fully submerged and instrumented toroidal horizontal platform (206) at a level below the "100-Year Horizon", which by some accounts is 500 meters but can be reasonably approximated by a 100 m. The 100-Year Horizon is a depth at which organic matter, crossing that depth, is not likely resurface during the following century. The elevational dampening of the spar buoy (201) is engineered so that elastic or inelastic tensions on the suspension cables are within acceptable limits during a lifetime of up to 6 months or more. Multiplicity in the design accommodates progressive failure without loss of the instrument packages (207). Periodic cable replacement is assumed, preferably by bringing the instrument assembly and spaceframe up from depth for inspection and maintenance. As an alternative to a rigid toroid (206), a spaceframe of structural elements, for example a tensegrity structure or space-filling truss, can be used to form the horizontal platform. The purpose of the horizontal platform or spaceframe at depth is to provide a means for quantitating net sediment fall or "rain", including cell aggregates and faecal pellets, through the 100-Year Horizon and comparing this to gross productivity of the SRC-seeded body of water. Samples of the particle sediment are analyzed for fixed carbon in order to validate carbon sequestration per unit time and to study diurnal or seasonal variations, or the effect of experimental parameters such as nutrient supplementation. A horizontal plane (210) forms the "sampling grid" or "transect line". In one embodiment, a fine mesh plankton net is stretched across the frame of the toroid, and robotic strainers vacuum up the filtrate at regular time intervals. In another embodiment, lasers and photodiode detectors are used to quantitate particle transits per unit time and particle size in the manner of a particle counter. A field of criss-crossing laser beam particle counters is conceived. Violet blue lasers (e.g. 465 or 472 nm) and green lasers (e.g. 532 or 543 nm) are useful and are selected here because the transparency of water in this wavelength range is reasonably good. Light in the laser beam is scattered by particles intersecting the beam; the time and scattering coefficients correlate with the size of the particle. Stacked spaceframes at different depths are also conceived. By linking multiple buoys together on the surface, the spaceframe can be suspended at multiple attachment points, permitting higher confidence in the determination of sediment fall parameters over the full grid area encompassed by the spaceframe, independent of ocean currents. Validated flux rates for carbon-rich sedimentary deadfall can be monetized as described below.

Figure 21:
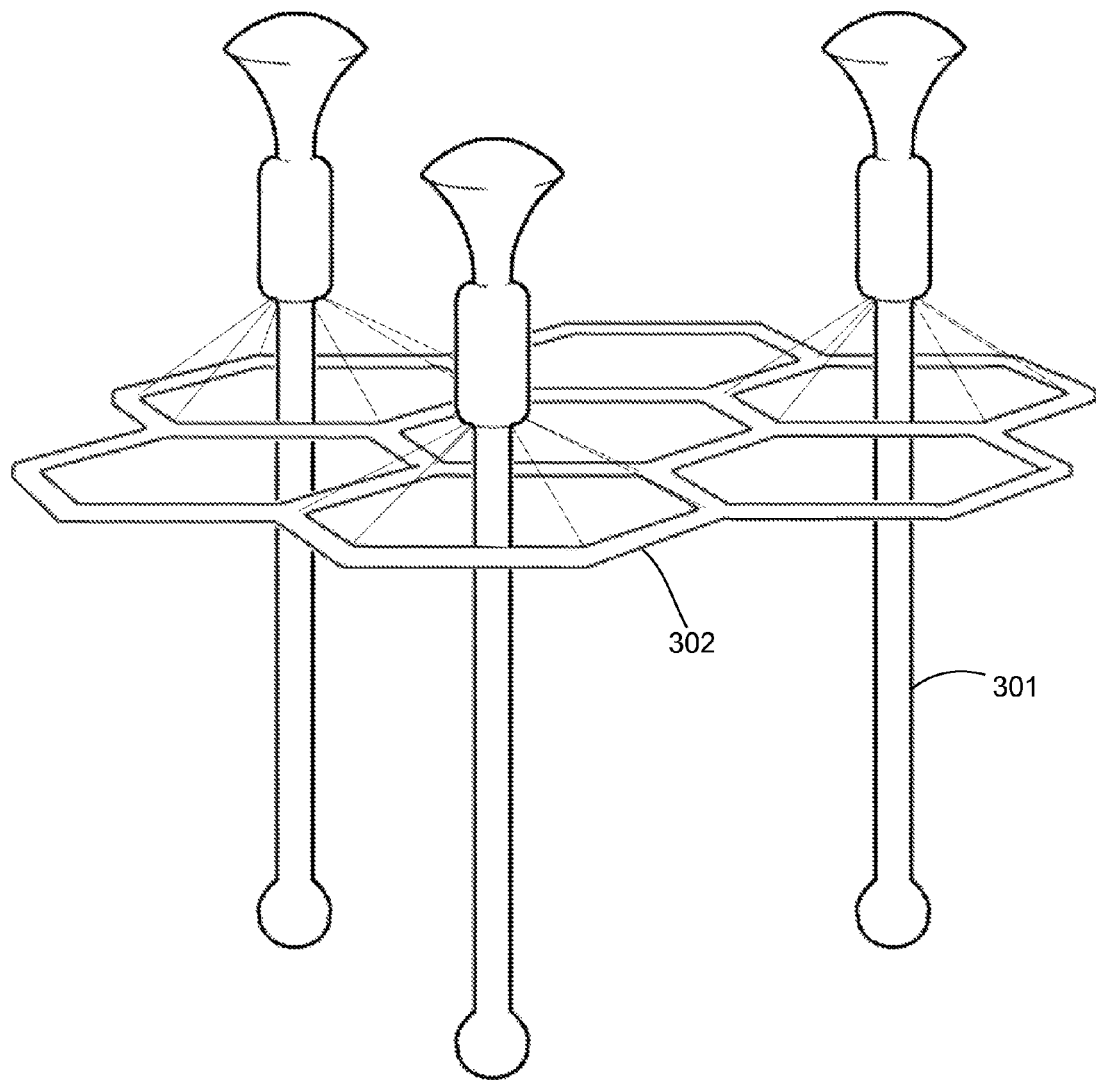
FIG. 21 is a view of a network of spar buoys supporting a hexagonal docking collar.

FIG. 21 is a view of a network 300 of spar buoys 301 supporting a rigid hexagonal docking grid 302. Shown are seven hexagonal cells and three spar buoys. The rigid cellular grid is suspended by cables from the buoyant spar buoys. The grid is a structural framework for positioning the spar buoys and may be configured to form a planar array or an annular array or network of spar buoys surrounded an enclosed surface area of an ocean. The spar buoys are surrounded on an outside periphery by a floating curtain to contain dispersed floating compositions within the enclosed surface area.

Figure 22:
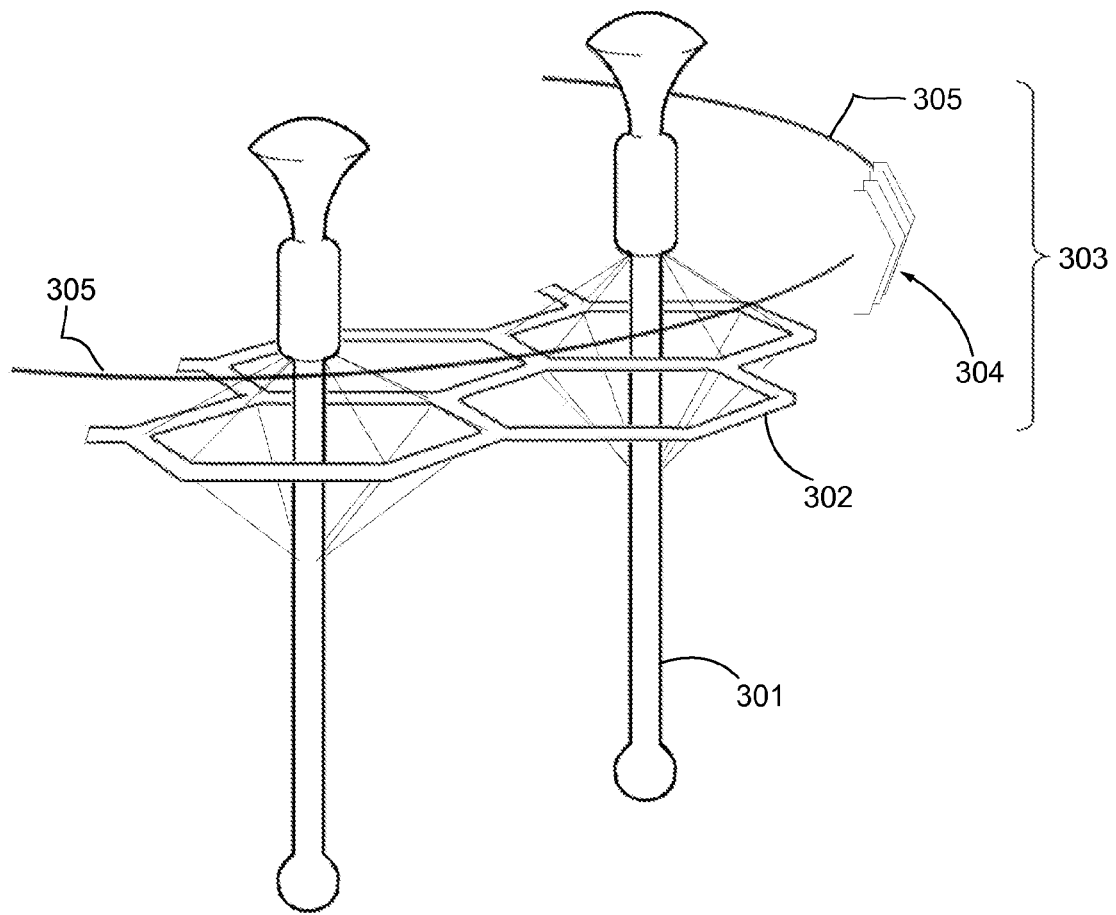
FIG. 22 is a partial view of a network of spar buoys with peripherally disposed wave energy dissipation barrier shown in part.

FIG. 22 is a partial view of a network of spar buoys 301 on docking grid 302 with peripherally disposed wave energy dissipation barrier 303 shown in part. As illustrated, the barrier 303 is a peripheral curtain of wave energy dissipating fins 304, four of which are shown here attached to a rigid circular member 305 that is typically supportedly associated with multiple spar buoys. Generally the fins form a barrier for diffusing wave energy, and are palisaded to surround the enclosed ocean surface and diminish the amplitude and peak/trough structure of waves that cross the barrier. Structure of a representative fin system is shown in more detail in FIGS. 23A and 23B.

Figure 23A:
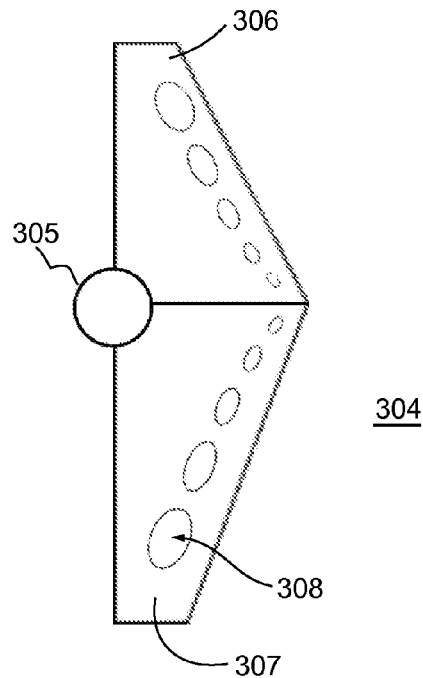
FIG. 23A shows a fenestrated wave energy dissipation fin.
Figure 23B:
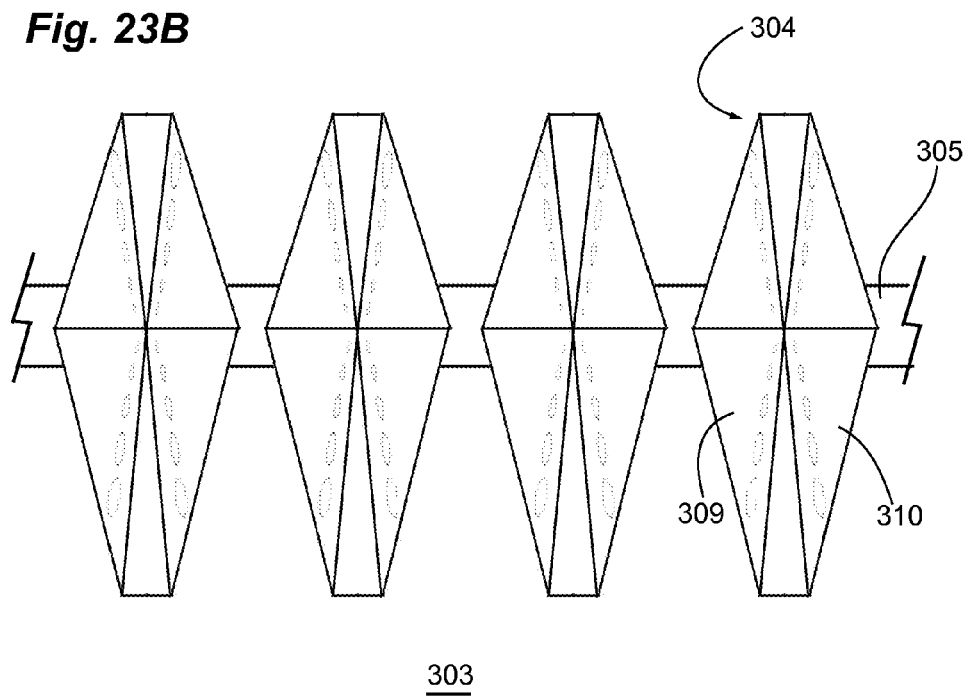
FIG. 23B depicts four fins palisaded on a rigid support to form a wave diffuser.

FIG. 23A shows a fenestrated wave energy dissipation fin 304. FIG. 23B depicts four fins palisaded on a rigid support to form a wave diffuser 303. Each fin includes an above-waterline 306 and a below-waterline section 307. The fins are attached at a equatorial waist to a rigid support beam or tube 305 that surrounds the spar buoy network. Contralateral walls (309, 310) of each fin define a hollow internal volume that tapers from the equatorial waist to an upper tip and a lower tip. Each wall is perforated (fenestrations 308), defining one or more openings for ingress of seawater. As a wave envelopes and passes through spaces between the fins, the energy of the wave is diverted by the fenestrations, retarding and diffusing progress of the waveform and thus reducing its peak-trough amplitude. Under moderate sea conditions, this device and related devices for diffusing wave energy serve to reduce strains on the cables joining the spar buoys to submerged grid or spaceframe members and the surrounding float systems that make up the "corral" surrounding the ocean area under study. The annular pontoons also act as wave dampeners for the central spar, increasing stability. Cooperative nested dampening elements and systems may also be used.

The wave energy dissipation system is generally disposed outside the enclosed study area, the wave energy dissipation system is for example a palisade of generally vertical fins, each fin having a leading edge facing the ocean, a trailing edge facing the enclosed surface area, and each fin defining a pair of fenestrated contralateral walls apposing each a next fin, wherein said contralateral walls of said each fin define therebetween an internal volume of open cells or baffles configured for progressively filling in a wave surge and progressively draining in a wave trough, and further wherein said palisade is supported from said spar buoy or network of spar buoys and has a height extending above and below the amplitude of wave.

The spar buoy or network of spar buoys are submersibly anchored to one or more retractable cables attached to the seafloor and a waterline of the spar buoy or network of spar buoys is configured with by adjusting flotation with pumps and by winching the spar buoy on cables attached to anchors on the seafloor. The floating surface boom or booms, and said wave energy dissipation system are generally attached to the spar buoys, either directly or indirectly, generally by multiple tethers.

The buoy or buoy network serves as both a marine productivity island and an instrument platform. The superstructure may be configured for aquaculture, aquacultural research, or for validation and monetization of sedimentary carbon sequestration. This apparatus is useful in a variety of methods which are further embodiments of the invention. Methods of the invention include a method for sequestering fixed carbon below the 100-Year Horizon of an ocean, which comprises dispersing a buoyant composition on the surface of the ocean, the buoyant composition comprising an inorganic nutrient or nutrient formulation in an inorganic sustained-release matrix, and a light reflective surface or cap that tends to orient itself skyward when floated. Also conceived is a method for increasing planetary albedo by dispersing on the surface of an ocean a composition having a light reflective surface and optionally an inorganic nutrient or nutrients in an inorganic sustained release matrix. Fortuitously, this results in cooler surface waters, which are recognized to result in increases in primary productivity.

In another aspect, the compositions and apparatus of the invention more generally are representative of compositions and apparatus for enhancing solar exsolation, where the amount of exsolative energy transferred from the terrestrial surface to a plane above the troposphere (generally taken as the layer of atmosphere extending from the earth's surface to the base of the stratosphere, about 10-16 km above the earth and marked by decreasing temperature as a function of altitude) is quantified and validated. By validating the energy flux or flux rate, for example in units of Joules or Joules per unit time, exsolation credits may be issued. Exsolation credits are financial instruments tied to a specific unit of energy transferred from the earth's surface to a plane above the troposphere, or more preferably above the stratosphere. The amount of energy transferred may be validated by satellite pyrometry or by mathematical modeling based on measurement of a terrestrial reflection and properties of the atmosphere in the path of the reflected light.

Exsolation credits are disbursed or traded, for example in a commodities market. A market for trading a solar exsolation credit instrument issued by the above apparatus will generally include a computer, the computer comprising a microprocessor, a volatile memory, a non-volatile read-only memory containing instructions for the microprocessor, a database containing records, the records comprising an ask price for a solar exsolation credit instrument and a bid price for a solar exsolation credit instrument, and a user interface for entering and displaying said records. The computer is generally programmed also to execute trades. Optionally a communications port is provided for remotely displaying ask prices, entering bids and confirming trades, as is generally familiar to those familiar with modern commodities markets. However, a market for a commodity, where the commodity is a heat transfer unit, is not a conventional market, and is useful to more fully assess the relative distribution of resources and labor between processes where the social benefit needs to be balanced against a heat output or a greenhouse gas output into the common atmosphere. For example, a process that results in conversion of a higher albedo surface to a lower albedo surface may not be commercially attractive if the total costs of global warming are added to the project; and by placing a cost on an equivalent discharge of heat from the terrestrial surface, the operator of the process has the option of ameliorating the damage only to the extent that the value of the product of the process exceeds the cost of the amelioration. And in this way, processes competing for exsolation credits are brought into a zero net sum market, which is required to be sustainable. Unsustainable processes that result in more heat than is balanced by available exsolative credits will not be profitable and will cease.

A process that results in greenhouse gases will, similarly, be required to either obtain equivalent reduction in greenhouse gases by other means, or to produce relief by causing to be produced solar exsolation equivalent to the net heating resulting from the release of greenhouse gases. Again the result is a selection pressure favoring sustainable processes. Not only must the social costs of greenhouse gas production and release be considered, but the global heating and cooling balance must also be considered in tallying social costs of processes, industries and markets. A market for exsolative credits may be modeled on a "cap and trade" system for carbon credits, and is complementary thereto.

Alternatively, carbon sequestration credits can be generated. Markets for trading carbon credits are generally well understood, but validation of those credits has been problematic. The apparatus of the invention is built specifically to validate carbon sequestration in sedimentary deadfall below the 100-Year Horizon of an ocean. This is a satisfactory criterion for issuance of a validated carbon sequestration certificate denominated in mass of carbon sequestered as $CO_2$ equivalent.

FIG. 24 describes steps of a method for using an apparatus of the invention to issue a validated carbon sequestration certificate.

The invention is also a method for validating and issuing carbon sequestration certificates on a scale large enough to effect global cooling in a single season. While not limited thereto, the following steps of the method may be practiced to achieve this result:

A. First having built a network or array of spar buoys for enclosing a surface of an ocean;
B. Dispersing a buoyant inorganic composition within the enclosed surface at a partial fill factor, the composition having a topology with microscopic and macroscopic niches;
C. Suspending from the network or array of spar buoys a space frame defining a 100-Year Horizon at a depth of 100 m;
D. Mounting an instrument package on the space frame for measuring sedimentary deadfall through the 100-Year Horizon;
E. Measuring and integrating flux of sequestered carbon per unit time;
F. Validating the flux of sequestered carbon crossing 100-Year Horizon; and
G. Issuing one or more monetizable or tradable carbon sequestration certificates, wherein each certificate has a denomination equivalent to a validated amount of sequestered carbon as $CO_2$ in the sedimentary deadfall as measured hereby.

Certificates from this operation are exchangeable for cash or services, or for other tangible value. In one embodiment of the invention, the validated carbon sequestration certificate (CSCert) itself can be deemed a product-by-process.

The apparatus may also include or be in linked operative communication with a data processing and communications system for registering or trading the certificates in a market or through a broker, which comprises at least one server of a network, said server comprising one or more processors, at least one volatile memory, at least one non-volatile read-only memory containing instructions for said processor or processors, and having a dataport operably connected to at least one database, said database containing records, wherein said records include an inventory of CSCert certificates that have been registered and are available for trading and their denomination. A network of this kind may also interactive displays for displaying the inventory and software tools and read-writable databases for managing the inventory of said certificates, recording ask and bid prices, recording trades, and for processing payments and credits, while not limited thereto.

EXAMPLES

Example 1

A 30 mL aliquot of a 10% (w/v) stock of Miracle-Gro (Scott's Miracle-Gro Products, Marysville Ohio) was added to 50 mL of colloidal silica in methanol (Nissan Chemical America, Tarrytown N.J., CAS 112926-00-8) and the mixture was heated in an open vessel to reduce the volume to about 40 mL. A clear solution resulted. The solution was then allowed to cool and a clear hard gel matrix resulted. Over time in an open container, a somewhat brittle solid formed.

A binder such as a sol-gel precursor is optionally used to semi-permanently fuse the colloidal silica, as is done in silica "hardcoat", a commercial process (see for example U.S. Pat. No. 6,587,263). Entrained air or $CO_2$ is also incorporated in the matrix.

Example 2

The following mineral components were crushed and mixed with a mortar and pestle.

| Major Inorganic Species | gms |
| --- | --- |
| Iron Oxide | 50 |
| Iron Nitrate | 10 |
| Calcium Oxide | 20 |
| Calcium Phosphate | 10 |
| Zinc Carbonate | 5 |
| Magnesium Oxide | 4 |

To 10 gm of the above mixture, the following trace mineral components were added with further grinding.

| Trace Inorganic species | gms |
| --- | --- |
| Copper Nitrate hemipentahydrate | 0.70 |
| Phosphomolybdic Acid | 0.20 |
| Manganese Chloride | 0.08 |
| Phosphomolybdic Acid | 0.01 |
| Cobalt Nitrate hexahydrate | 0.01 |
| Boric Acid | 0.005 |
| Selenium Chloride | 0.001 |
| Sodium Vanadate | 0.001 |

To this mixture of solids, 200 mL of colloidal silica in methanol was added. After heating with stirring to reduced volume and cooling, a hard gel formed. This gel when baked produces a rock-like composition without the decomposition indicative of organic charring.

Example 3

As a first approximation, mix the aqueous suspension of Example 2 with 200 mL of colloidal silica in methanol as described above. After heating with stirring to reduced volume, add 300 gm of glass hollow microspheres and continue stirring until fully mixed. Charge 50 mL iron molds with the mixture, the molds having a selected shape and depth, with a shallow conical bottom profile. Bake to lithification.

During the early stages of baking, it is anticipated that the iron filings will sediment to the tip of the base of the mold and the glass hollow microspheres will rise to the surface of the liquid. This results in a "puck" shaped siliceous ingot on ejection from the mold. The ingot is comprised of highly dispersed inorganic minerals, sedimented iron filings, and a froth of microbubbles in a silicate matrix. In other words, puck density is here preferably non-uniform but is cumulatively less than that of water, that is to say the aggregate density is less than 1 $gm/cm^3$. By optimizing the temperature, baking time, and ratio of solids to glass microspheres, a floating puck is formed.

Example 4

The following mineral components are crushed and mixed with a mortar and pestle.

| Inorganic species | gms |
| --- | --- |
| Iron Oxide | 30 |
| Iron Nitrate nonahydrate | 20 |
| Calcium Oxide | 20 |
| Calcium Phosphate | 5 |
| Magnesium Carbonate | 15 |
| Zinc Oxide | 5 |

To 10 gm of the above mixture, the following trace mineral components are added with further grinding.

| Species | gms |
| --- | --- |
| Copper Sulfate | 1.2 |
| Ammonium Molybdate | 0.6 |
| Manganese Oxide | 0.1 |
| Cobalt Nitrate hexahydrate | 0.01 |
| Boric Acid | 0.002 |
| Selenium Chloride | 0.001 |
| Vanadium Chloride | 0.0001 |
| Nickel Chloride | 0.0001 |
| Chromium Chloride | 0.0001 |

To this solid powder, 300 mL of colloidal silica in water (Snowtex-N, Nissan Chemical Industries, Tokyo Japan) and 400 mL Perlite are added. The slurry is quickly mixed in a wiper-type rotary mixer and extruded as coarse gel pellets into a furnace designed with modification from the teachings of U.S. Pat. No. 4,257,799. Brief exposure to temperatures of about 1000° C. results in a glass coating on the pellets. By adjusting transit temperatures and times in the furnace, a hard, pelletized inorganic composition having a density of less than 1 $gm/cm^3$ results. The pellets readily disperse when floated on water and are sufficiently buoyant as to provide a strongly retroreflective substrate.

Similar results can be obtained through the use of blowing agents which decompose at elevated temperature (for example urea at temperatures exceeding 600° C.) without the need for Perlite or glass hollow microspheres. The resultant products contain no organic components, the blowing agent having been decomposed to inorganic components (in the case of urea, carbon dioxide and ammonia). Gas injected into molten glasses also results in floating glass "pellets", sensu lato. Methods for rapid thermal processing are favored so as to limit gaseous diffusion in the matrix during processing.

Example 5

A formulation development sequence is undertaken which results in a mineraline composition in a glass or crystalline flotational matrix that favors the growth of diatoms.

Example 6

A formulation development sequence is undertaken which results in a mineraline composition in a glass or crystalline buoyant matrix that favors the growth of coccolithophorids.

Example 7

A formulation development sequence is undertaken which results in a fractal, porous mineraline substrate in a glass or crystalline flotational matrix that favors the establishment of a complex food chain of primary producers grazers, and higher trophic levels.

Example 8

A formulation development sequence is undertaken which results in a glass or crystalline flotational composition that enhances the albedo of planetary surface bodies of water.

Example 9

In support of the development sequences of Examples 5, 6, 7, and 8, an ocean buoy of FIG. 5 or 6 is designed and anchored at a suitable field study site. Data collected in the field include insolation and reflected radiation, gross and net sequestration in sediments, primary production, and harvestable fish yields, comparing different formulations.

Also evaluated in the field are the weatherability and leaching rates of the formulations, although preliminary evaluations are typically made in stirred vessels of the sort used by the pharmaceutical industry to measure tablet dissolution.

Example 10

A modified stoneware clay is mixed as follows:

| Composition | lbs |
|---|---|
| Water | 28 lb |
| Fireclay: | 41 lb |
| OM4 Ball Clay: | 24 lb |
| Kaolin: | 10 lb |
| Silica Powder: | 10 lb |
| Sodium Silicate 40% (v/v): | 20 lb |
| G-200 Feldspar | 10 lb |
| Fe, Mg, Ca, Zn and trace elements | 10 lb |

The mixture is mixed with forced injection of air or $CO_2$ and extruded into a ribbon. During firing, the green ceramic ribbon is coated with a glass mixture of titanium oxide and silica dioxide or magnesium fluoride. An inorganic gas precursor such as urea is included. As a practical matter, it may be useful to include fibers for tensile strength, such as those of Kevlar® (Dupont, Richmond Va.), glass wool, carbon fibers, graphite, gypsum, or polyester. Larger structures can be made by applying the clay over a cementitious vessel composed of Sorel Cement or Portland Cement.

A light diffusing glass contains soluble contaminants of the glass that crystallize at a lower temperature, producing a so-called opal or alabaster glass, by homogeneous nucleation. Semi-crystalline ceramic bodies with voids may also be made by combining finely divided particles of corundum, mullite, quartz, and argillaceous or siliceous materials, optionally with grog, before firing or sintering. Fused quartz is well known as a glass. TiO2 is used as an opacifying agent in glass. A large number of glass compositions may be made by combining three basic components, SiO2, Al2O3 and one or more basic metal oxide selected from MgO, CaO, ZnO, CdO, MnO, FeO, CoO and NiO. These include soda-lime silica, which is composed of mixtures of silica, soda, lime alumina and magnesia and optical glass, which typically contains only silica and soda. Other minerals may also been included. When also mixed with Na2O or K2O the solubility of the glass may be controlled. These are formed as cullet and are typically melted in a furnace and drawn or rolled to form plates, but by compounding the cullet with a gas precursor such as urea, exploded voids can be formed to reduce the density of the body. Also included are oxide glasses not based on silica, which include phosphates and borates and have use in time-release formulations, and combinations thereof.

Various formulations based on "cement" are also used. Cement can most broadly be considered to be a family of chemically bonded ceramics. Cements, which may have a calcium oxide, calcium silicate, aluminum oxide, or a magnesium oxide base, with minor amounts of other metal and alkaline metal oxides, and optionally with gypsum as a retardant, without limitation thereto, may be cured by adjusting hydration, pH and by heating, but also may be cured by exposure to carbon dioxide, resulting in a hard, dense carbonate shell. Early patent literature related to this process includes U.S. Pat. Nos. 1,932,150, 2,496,895, 2,877,499, 3,204,019 and as described by Schulze in U.S. Pat. No. 3,356, 779, it is shown that a mixture of hydrated cement and silica sand, when exposed first to about 20% or more of carbon dioxide in an enclosed chamber for an initial set and then to steam forms hydrated calcium silicates of use in the building trades. Water is commonly limited in the initial mixture to 5-30%, although slurries, also termed "wet mix", may also be used. It is reported that higher pressures of $CO_2$ result in better results. Steam is applied in an autoclave. As with glasses, exploded cements may also be used. Exploded cements may be made by supersaturating the plastic precursor with a partially soluble gas or with a gas precursor that is subsequently decomposed or caused to come out of solution. By adding an excess of $CO_2$ to a wet cement precursor, the initial set will include many gaseous voids that are not filled during subsequent processing so that the final product is buoyant. Refinements of this process are the subject of U.S. Pat. Nos. 4,069, 063, 4,093,690, 4,117,060, 5,518,850, 5,518,540. As adjunct accelerants for use with $CO_2$, calcium chloride, magnesium chloride, HCl, H2SO4, H2PO4 and HNO3 may also be used. Sodium carbonate, sodium bicarbonate, marble and calcium carbonate may also be used. Clays, pumice, crushed scoria or fly ash may be used to reduce the free water content. Thus the use of $CO_2$ to modify the properties of cement and cement-like products is well known.

Jones in U.S. Pat. Nos. 5,518,540 and 5,965,201 uses supercritical $CO_2$ to treat cement matrices after curing. $CO_2$ is supercritical at greater than 1000 psi at about 3° C., and behaves as a liquid and a gas, more readily penetrating cement, and reducing naturally alkaline cement to near neutral pH, thus changing the chemistry of the final product. Other supercritical solvents may also be use, such as short chain hydrocarbons, sulfur hexafluoride and nitrogen. Further disclosed is a process for treating cement precursors with $H_2O_2$ to produce a foam-like matrix that is subsequent to curing, hardened with scCO2, such as from a mixture containing fly ash, 5% $H_3PO_4$ in water, and either MgO or CaO (60:32:5) with up to 3% $H_2O_2$, or from a mixture of granitic quarry fines, cemented with lime, high-aluminate pozzolan, water and hydrogen peroxide, which are further cured with scCO$_2$, forming porous cores that are very light. Because the process absorbs $CO_2$, it offsets a portion of $CO_2$ released during manufacture of Portland cements used as feedstocks in the process.

Example 11

Perlite floated in an inorganic algal growth medium in a Petri dish was heavily and rapidly colonized by mixed populations of algae and diatoms after inoculation with soil or pond water. This primary producer population was soon joined by grazers and heterotrophic species.

Example 12

As a full scale field demonstration, a prill [nozzle extruded] of mineral:silica glass formulation impregnated with microbubbles is released into the equatorial Pacific Ocean in an area of offshore flow from Peru, from which it disperses in a generally east to west track by the action of currents as a plume larger than the size of New Zealand. The material has a half-life of 1 year and contains iron, calcium, magnesium, zinc, and trace copper, molybdate, manganese, cobalt, borate, selenium, vanadium, and nickel, supplemented with nitrate, phosphate, and with blowgas enriched in $CO_2$. The free-flowing, buoyant prill particles are designed to promote growth of phytoplankton, increase higher trophic levels and complexity, increase sedimentary deadfall of fixed carbon, and to have sustained release properties.

Production is assumed to be 2 million metric tons annually. Cost per metric ton of raw material is on the order of $20 US FOB. Plant capacity is expected to cost US$25-50M. Energy capacity for operating the plant is on the order of 20 MW, at a cost of $50 to $100 per MWhr. These figures are based on US production of an analogous material termed in the trade, "perlite", such as is used extensively in horticulture and insulation.

If dispersed at 5 gm per meter squared, production is sufficient to cover 360,000 square kilometers of ocean. Reaching the central pacific in about 3 months, the material acts as snow or ice, reflecting incident sunlight. An increase of 0.05 in albedo is obtained. An immediate decrease in surface temperature in the plume due to the increased albedo is estimated from the Stephan-Boltzmann equation, assuming pseudo-adiabatic surface layer cooling. The calculated value is a reduction in SST of 2.9° C., based on a reduction in insolation absorbed by the ocean water of 17 Watts/m$^2$. Because ENSO events are associated with 4° C. increases in central warm pool Pacific Ocean temperatures, this 2.9° C. cooling is highly significant. A similar drop in air temperature over the affected body of water is also noted. As an immediate result: 1) an ENSO event predicted for that year is significantly reduced in intensity; 2) there is no drought in Australia that year; 3) the expected El Niño off Chile does not materialize, 4) the Humboldt current continues with offshore flow and ocean upwelling, 5) contributing indirectly to good fishing that year. No harm is done, and the material has essentially vanished in less than 3 years.

Furthermore, by increasing net sedimentary benthic export of fixed $CO_2$ to 3 gm $CO_2/m^2$/day in the plume, an annualized deadfall (fixed carbon to the benthos) of 275 tC/km$^2$/yr is feasible. In a plume of 360,000 km$^2$, 0.4 Gt $CO_2$ is exported below the 100-Year Horizon over a year. A validated flux of 0.4 Gt $CO_2$ per year, sold in the form of carbon sequestration certificates, conservatively assuming a starting value of $10/ton, is expected to realize $40 billion US per year, sufficient cash flow to fund operations and to make payments to a licensing body. A sequestration process continuously driving 0.4 Gt $CO_2$ from the atmosphere each year is expected to have a detectable global cooling effect. When sufficient global cooling has been achieved, the apparatus can be dismantled and drydocked until again needed with no lasting harmful effects.

The cooling effect is multiplied by synergic effects. Following release, the sulfur cycle is studied. As surface mixing decreases in the plume, DMS production increases significantly, resulting in increased kumogenesis extending thousands of miles downstream, generally westerly, from the plume. A noticeable cooling of the earth that season is observed as the result of the de novo stimulation of cloud formation over the Pacific.

In this example, the rate of release of nutrients from the prill is determined by the leachable counterion content of the glass. Calcium oxide will desolubilize glass, and monovalent anions such as potassium oxide will increase it. By adjusting the ratio of divalent to monovalent cations in the glass, its solubility and rate of leaching can be controlled. The ratio of cross-sectional area to surface area is also a factor in controlling leaching. By modifying the underside of the prill in a floating matrix such as an extruded ribbon cut to suitable lengths, increased biological habitat can be obtained. Increases in primary production are also associated with increases in production of harvestable species. Buoyant SRC prill may also be made from foamed or exploded clay, such as kaolin, which is far more abundant than perlite glass.

Example 13

It has been shown experimentally that increases in albedo can force large scale local cooling. In a recent publication, Campra (2008, J Geophys Res 113:1-10) reported a long term study of 26,000 hectares in southern Spain, where installation of greenhouses, in what is described as "a continuous greenhouse-covered surface," has resulted in a positive increase in albedo of about 0.1. This increased albedo was associated with reflective heat transfer averaging −20 W/m$^2$ (i.e., cooling) by MODIS satellite infrarometry. Aerial photos confirm that the surface is extensively whitened by whitewashing the glass roofs of the structures. Terrestrial solar radiation IN is about 340 W/m$^2$; therefore a reflective component of 20 W/m$^2$ OUT is highly significant if integrated over a large enough surface area.

In short, surface albedo can be used to reverse global warming. A plume of floating pelagic reflective pucks, dispersed across the equatorial oceans over an area of 2.2×10$^6$ km$^2$, a surface area the size of Greenland, and resulting in a change in albedo of +0.1, will result in perceptible global cooling in a matter of days or weeks, as can be verified by MODIS satellite infrarometry. Taking global surface insolation at 45 PW, the net effect of 20 W/m$^2$ forced cooling by reflection to space over this surface area (44 GW) is an essentially instantaneous −0.1% change in the global surface net energy balance.

Interestingly, assuming a total urban landscape of about $2.2 \times 10^6$ $km^2$ and an increase in albedo of just 10% (as by whitewashing all roofs and roads or by installing white vinyl roofing and high albedo pavement), a similar degree of cooling will be achieved. Thus an apparatus for achieving solar exsolation will include a reflective surface and a means for validating the amount of solar exsolation. The dispersable reflective compositions disclosed here have multiplier effects: increasing albedo, increasing marine productivity, and increasing sedimentary deadfall. Enhancement of annualized pelagic sedimentary deadfall in a plume of similar scale is calculated at about 0.6 GtC, almost 10% of human $CO_2$ release by fossil fuel consumption (currently 7 GtC annually); further compounding the global reflective cooling effect of the compositions.

Example 15

Figure 25:
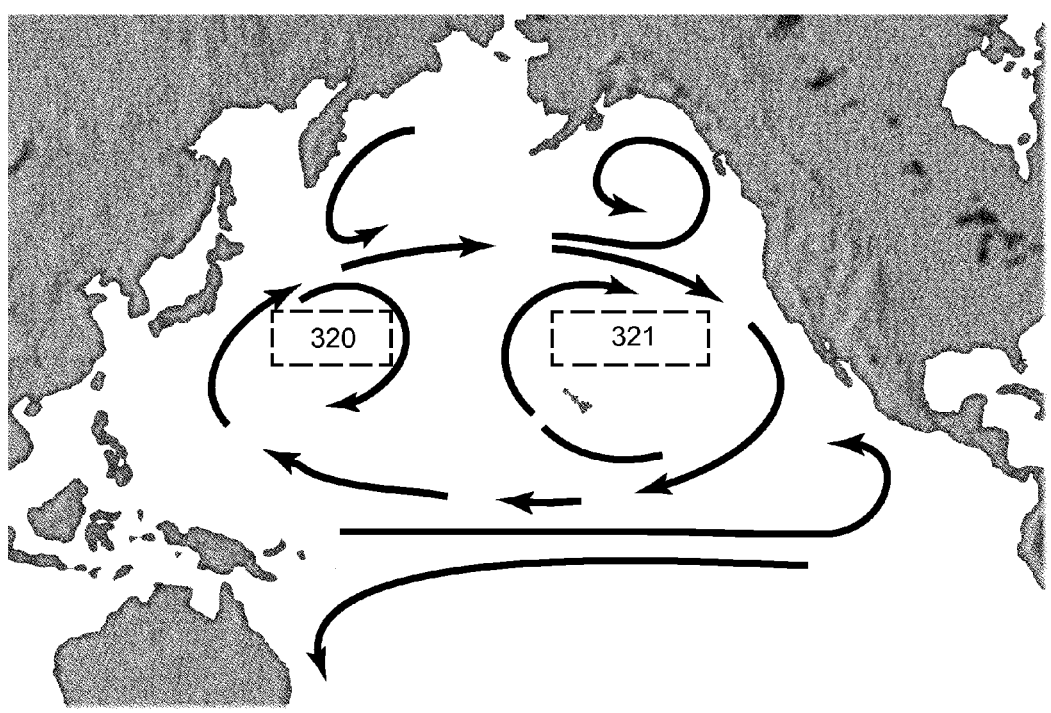
FIG. 25 illustrates areas of the northern pacific characterized by relatively calm water and a convergence zone where microparticulate plastic is known to have accumulated. Boxes (dashed lines) indicated preferred area for deployment of an apparatus for bioremediation combined with issuance of carbon sequestration certificates as required to support operating expenses.

FIG. 25 illustrates areas of the northern pacific characterized by relatively calm water and a convergence zone where particulate plastic is known to have accumulated and is resisting degradation. These areas are gyres. Boxes (dashed lines 320, 321) indicated preferred area for deployment of an apparatus for bioremediation combined with issuance of carbon sequestration certificates as required to support operating expenses.

A large mass of municipal solid waste has been discovered to be accumulating in oceanic gyres, particularly the North Pacific Gyre, which covers about 17 million square kilometers of ocean. It is believed that about 10% of metropolitan and marine sewage reaches the oceans and about 30% of that is plastic and degrades with a half life of several hundred years.

The largest concentrations of garbage are found northeast of Hawaii, about halfway between Hawaii and the western coast of the mainland of the United States of America. Most of this waste is associated with a standing high pressure area of calm water, a sub-tropical convergence zone (321) shown in FIG. 25. A second convergence of waste (320) is found west of the coast of Japan. Other eddies where indigestible matter has accumulated are found in all the oceans.

All gyres share a becalmed central section of water that has historically been avoided by both humans and many animals. The slow moving waters of the convergence zone have caused sailors to avoid them. The desert-like ecosystem, with limited tropic layer complexity, also makes them poor habitats for predators.

Plastic, which degrades slowly, is selectively accumulated in the gyres. In one study, about $3.5 \times 10^5$ pieces of plastic was found per kilometer squared, having a mass of about 5 $kg/km^2$, the "garbage patch" covering millions of square miles of ocean. Plastic was about six times more concentrated than biomass in the water.

The calm water of the eastern fringe of the North Pacific Gyre, north/northeast of Hawaii in the area of 321, is a preferred site for deploying a spar buoy network of the invention. For study purposes, spar buoys are formed into a hexagonal array or docking grid and extended to enclose a patch of water totaling several kilometers in surface area. A buoyant, inorganic, sustained-release nutrient composition of the invention is dispersed inside the study area. Advantageously, the apparatus need not be anchored and remains in the gyre by the action of the ocean currents. The nutrient medium is formulated to accelerate entrapment of plastics into dense aggregates that sink and also to promote a biological pump for transferring carbon from the atmosphere to the oceans depths, which is in the range of 6000 meters in this part of the ocean.

Suspended from the spar buoy network are one or more spaceframes at a depth of about or slightly greater than 100 meters, as generally corresponds to a 100-Year Horizon. Laser particle counters are mounted on the spaceframe so that particles can be counted and sized by methods known in the art relating to suspended particle characterization. By analyzing selected samples chemically, a correlation index between laser particle counts and distribution versus carbon content is readily determined. Carbon content in the form of biologically fixed carbon has a relatively constant ratio to particle mass when averaged over time. Continuous real time measurement of the flux of sedimentary deadfall across the 100-Year Horizon is then monitored, validated and reported. The flux can be integrated and converted to equivalent carbon dioxide mass. A validated certificate is issued having a denomination in units of carbon mass as $CO_2$ equivalents. This certificate may be monetized or traded, and used for example to drive up the cost of pollution by requiring that $CO_2$ emitters purchase a quantity of carbon sequestration certificates sufficient to compensate for or exceed the quantity of $CO_2$ emitted.

In an enclosed surface of 360 $km^2$, about 0.04 Gt $CO_2$ is exported below the 100-Year Horizon over a year. A validated flux of 0.04 Gt $CO_2$ per year, sold in the form of carbon sequestration certificates, conservatively assuming a starting value of $10/ton, is expected to realize $40 million US per year, sufficient cash if supplemented with grant monies to fund operations and support scientific research. Research at this scale is directly scaleable to larger installations if desired.

Parenthetically, if an array of the invention was constructed to cover the entire convergence zone, and area of 17 million square kilometers, assuming sediment production of 200 $tC/km^2/yr$, a biological pump having a flux of 3.4 GT/C per year (or 13.6 GT $CO_2$ per year) of sequestered carbon is possible. This is the largest known "quick fix" that has been proposed for rapid climate reconstitution in the event of a planetary crisis, has the potential to roll back decades of carbon dioxide buildup in the atmosphere, to reverse acidification in the ocean, and remains safe and can be rapidly dismantled when no longer needed. Compared side by side with point source remediation by terrestrial carbon sequestration, such as the alkaline carbonate method proposed by Zimmerman in U.S. Pat. No. 7,457,758, there is really no comparison. The present invention is the only known solution to climate change that can be scaled linearly to meet the planetary challenge described in FIG. 1.

Shipping channels may be constructed to reduce inefficiencies in marine transport. The point is again made that the compositions of the invention need not be corralled within a fence to be effective. A preferred solution is to release a free-floating, sustained release nutrient composition that is rich in niches and habitat onto the ocean currents, and continue release until a cooling trend is obtained.

Because the compositions are buoyant, it would be expected that these compositions shall accumulate in the gyres without need for enclosure. However, for scientific rigor and so that suitable instrument platforms can be suspended at the 100-Year Horizon (as useful for sedimentary deadfall validation studies), the spar buoy network provides the needed buoyant superstructure and the enclosure provides reassurance that the compositions will not be widely dispersed on the oceans without initial pilot studies, data collection on a small scale of a few square kilometers, and rigorous scientific review. The spar buoys also provide navigational aids to route ship traffic around the study site(s).

Interestingly, bioremediation is also feasible with the inventive apparatus. By stimulating biomass in the areas of garbage accumulation, emergent properties appear that are not evident at low biodensity. Exogenous particles are entrained in layers or clumps of gel and biomass in a complex, multilevel community, which includes extracellular capsular materials secreted by a wide range of microorganisms; and as these clumps become associated with calcareous or siliceous growths, the mass becomes dense enough to sink. Barnacles for example, are known to festoon a plastic bottle and drag it down. Plastic ingested by larger organisms is more likely to be entrained with macroscopic fecal matter that sinks below the 100-Year Horizon. While it can be argued that plastic residue on the ocean floor is disadvantageous, a steady rain of mixed sediment is expected to bury the material, leading ultimately to lithification and subduction over thousands of centuries, a satisfactory solution absent a realistic temporary option for recycling or for arresting the material at its source.

The carbon sequestration effect of the apparatus is synergic with any reflective properties that are inherently a property thereof. At full scale deployment, the reflective effects are significant on a planetary scale. Nonetheless, the carbon sequestration certificate is a useful financial tool in its own right for funding development and deployment.

The invention is not a scheme for weather modification, it is a system for biophysical engineering of global climate, and provides an apparatus, methods, and experimental framework for development of solutions to global warming. The systems disclosed herein are fully and/or prophetically conceived to be effective and safe.

Example 16

The invention in one aspect is a validated certificate of carbon sequestration having a denomination in carbon mass or moles and a market for trading same. In various embodiments, this invention pertains to a method and system of generating and trading a $CO_2$ certificate or commodity that is correlated to a quantified amount of $CO_2$ sequestered in a $CO_2$ sequestering product (biomass as sedimentary downfall). An equivalent certificate or commodity denominated in mass or moles of atomic C is also envisaged. The invention also pertains to a computer-implemented method and system of generating and trading the $CO_2$- or C-denominated commodity, and a program product comprising embedded instructions for causing the computer system to generate and trade the $CO_2$ commodity. The invention also pertains to the tradable $CO_2$- or C-denominated certificate itself.

In various embodiments, the system comprises a computer-implemented system of trading a $CO_2$ commodity, comprising: a $CO_2$ sequestration converter that is programmed to convert a quantified amount of $CO_2$ sequestered in a $CO_2$ sequestering product into a tradable validated certificate (CSCert). Tradeable instruments include but are not limited to: a Verified Emissions Reductions unit (VER), a Carbon Financial Instrument (CFI), a European Union Allowance (EUA), a Certified Emission Reduction unit (CER), an Emission Reduction Unit (ERU), a Voluntary Carbon Unit, or a carbon sequestration certification (CSCert).

In various embodiments of the system, a $CO_2$ sequesterer or a $CO_2$ regulator issues the tradable commodity; in some embodiments, the $CO_2$ sequesterer issues the tradable commodity based on the quantified amount of $CO_2$ in the $CO_2$ sequestration product; in some embodiments, a $CO_2$ generator, a $CO_2$ trader or the $CO_2$ sequesterer acquires the tradable commodity.

In another embodiment of the system, the tradable commodity permits the holder to emit a restricted amount of $CO_2$; in various embodiments, the tradable commodity is valid for a limited time. In various embodiments, the tradable commodity is priced based on the supply and demand for the tradable commodity in a commodity market; in other embodiments, the tradable commodity is priced based on the amount of $CO_2$ in the environment. In another embodiment, the $CO_2$ sequesterer may transfer the tradable commodity to a third party; in some embodiments, the $CO_2$ generator may retire the tradable commodity.

In various embodiments, the system may perform any of the following functions: receive payment for the tradable commodity; issue a receipt for purchase of the tradable commodity; or manage the inventory of tradable commodity. In various embodiments, the system comprises a computer network having GUI (graphical user interfaces) disposed therein.

In one embodiment, the computer program product comprises a computer installable medium comprising computer readable code embodied therein for causing a computer to execute a program module, comprising: a $CO_2$ sequestration converter that is programmed to convert a quantified amount of $CO_2$ sequestered in a $CO_2$ sequestering product such as sedimentary deadfall into a tradable commodity. In various embodiments, the $CO_2$ sequestration converter comprises computer-executable instructions for receiving data comprising sequestered $CO_2$; calculating a quantity of tradable commodity based on the sequestered $CO_2$; and issuing instructions for producing the tradable commodity.

In another embodiment, the system pertains to a computer-implemented system of trading a CSCcert certificate, which comprises: (a) a communication module comprising: (i) a input manager for receiving commodity request information and payment from a customer; iii) an output manager for providing a tradable commodity to a user; and (iv) a user interface manager for transferring information about tradable commodities between a user and the system; and (b) a processing module configured to execute transactions with a customer, wherein the processing module is configured to provide at least one of the following features: a transfer manager configured to transfer commodities to a customer; an inventory manager configured to register changes to the inventory of tradable commodities available for transfer; or a receipt manager configured to receive payment from a customer and issue a receipt to said customer indicating a successful transaction. The tradable commodity represents a quantified amount of $CO_2$ sequestered in a biomass below the 100-Year Horizon of an ocean.

All of the U.S. patents, U.S. patent application publications, U.S. patent applications, foreign patents, foreign patent applications and non-patent publications referred to in this specification and/or listed in the Information Data Sheets, are incorporated herein by reference, in their entirety. Aspects of the embodiments can be modified if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the specifics of the disclosure.

I claim:

1. An apparatus for validating sequestration of carbon below the 100-Year Horizon of an ocean and issuing a monetizable or tradeable carbon sequestration certificate having a denomination based on the mass of carbon sequestered therebelow, which comprises:
   a) a spar buoy or network of spar buoys, each spar buoy with vertically elongate hollow body having a first end with superstructure and a second end with ballast mass, said hollow body having an upper fixed displacement volume (V1) and a lower variable displacement volume (V2);
   b) a horizontally disposed spaceframe suspended from said spar buoy or network of spar buoys at a depth at or below the 100-Year Horizon of said ocean;
   c) an immersible analytical apparatus mounted on said spaceframe for measuring sedimentary deadfall data as an index of flux of sequestered carbon descending below the 100-Year Horizon of said ocean;
   d) a surface boom for enclosing a surface area of said ocean associated with said spar buoy or network of spar buoys;
   e) a composition dispersed within said enclosed surface area, said composition comprising an inorganic nutrient formulation in an inorganic, sustained-release matrix, said composition having a net aggregate positive buoyancy; and
   f) a computer-implemented system operatively connected to said analytical apparatus and configured for integrating and reporting flux of sequestered carbon descending below the 100-Year Horizon per unit time and issuing one or more monetizable or tradable certificates, wherein each certificate has a denomination equivalent to a validated amount of sequestered carbon as $CO_2$ in the sedimentary deadfall descended from said enclosed surface area to below the 100-Year Horizon of said ocean.

2. The apparatus of claim 1, further comprising a data processing and communications system for registering or trading said certificates in a market or through a broker, which comprises at least one computer of a network, said computer comprising one or more processors, at least one volatile memory with database, said database containing records, wherein said records include an inventory of certificates that have been registered and are available for trading and their denomination, and at least one non-volatile read-only memory containing computer readable code embodied therein for causing said computer to execute a program module comprising registering and inventorying said certificates and executing or assisting in execution of trades in said certificates.

3. The apparatus of claim 2, further comprising at least one interactive display for displaying an inventory or a record of a trade.

4. The apparatus of claim 2, wherein the system is configured for recording ask and bid prices, recording trades, and processing payments and credits.

5. A method comprising:
   a) floating an apparatus of claim 1 in an ocean, whereby a surface area of said ocean is enclosed;
   b) dispersing said composition in said enclosed surface area, wherein said composition is an inorganic nutrient formulation in an inorganic, sustained-release matrix, said composition having a net aggregate positive buoyancy;
   c) measuring sedimentary deadfall data as an index of sequestered carbon flux descending from said enclosed surface area to below the 100-Year Horizon of said ocean;
   d) integrating sequestered carbon flux descending below the 100-Year Horizon per unit time from said enclosed surface area and issuing one or more monetizable or tradable certificates, wherein each certificate has a denomination equivalent to a validated amount of sequestered carbon as $CO_2$ in the sedimentary deadfall descended from said enclosed surface area to below the 100-Year Horizon.

6. The apparatus of claim 1, wherein said superstructure comprises a pelagic aquaculture workstation.

7. The apparatus of claim 6, further comprising harvesting a sustainable yield of a higher trophic level biomass from said surface area of said ocean associated with said spar buoy or network of spar buoys.

8. The apparatus of claim 1, wherein said network of spar buoys comprises a planar array or an annular array of spar buoys.

9. The apparatus of claim 1, wherein said spar buoy or network of spar buoys, and said floating surface boom or booms, are submersibly anchored to one or more retractable cables attached to the seafloor and a waterline of said spar buoy or network of spar buoys is configured with pumps and winches.

10. The apparatus of claim 1, wherein said apparatus is not anchored and is retained in a gyre by the passive circulation of currents.

11. The apparatus of claim 10, wherein said composition dispersed in said enclosed surface area is formulated to accelerate bioremediation of plastic waste in said gyre.

* * * * *